(12) United States Patent
Amiri

(10) Patent No.: US 10,172,585 B2
(45) Date of Patent: Jan. 8, 2019

(54) TRACKING SYSTEM FOR IMAGING MACHINES AND RELATED APPARATUS

(71) Applicant: Torus Biomedical Solutions Inc., Vancouver (CA)

(72) Inventor: Shahram Amiri, Vancouver (CA)

(73) Assignee: Torus Biomedical Solutions Inc., Vancouver (CA)

(*) Notice: Subject to any disclaimer, the term of this patent is extended or adjusted under 35 U.S.C. 154(b) by 0 days.

(21) Appl. No.: 15/833,313

(22) Filed: Dec. 6, 2017

(65) Prior Publication Data

US 2018/0249982 A1    Sep. 6, 2018

Related U.S. Application Data

(63) Continuation of application No. 15/028,100, filed as application No. PCT/CA2014/050986 on Oct. 10, 2014, now Pat. No. 9,867,588.

(60) Provisional application No. 61/889,473, filed on Oct. 10, 2013.

(51) Int. Cl.
     *A61B 6/00*      (2006.01)
     *A61B 34/20*     (2016.01)

(52) U.S. Cl.
     CPC .......... *A61B 6/547* (2013.01); *A61B 6/4405* (2013.01); *A61B 6/4441* (2013.01); *A61B 6/487* (2013.01); *A61B 6/584* (2013.01); *A61B 2034/2048* (2016.02); *A61B 2034/2059* (2016.02)

(58) Field of Classification Search
CPC ..... A61B 6/547; A61B 6/4405; A61B 6/4441; A61B 6/487; A61B 6/584; A61B 2034/2048

USPC .......................................... 378/193–198, 207
See application file for complete search history.

(56) References Cited

U.S. PATENT DOCUMENTS

| | | |
|---|---|---|
| 6,049,582 A | 4/2000 | Navab |
| 6,200,024 B1 | 3/2001 | Negrelli |
| 6,285,902 B1 | 9/2001 | Kienzle, III et al. |
| 6,477,400 B1 | 11/2002 | Barrick |

(Continued)

FOREIGN PATENT DOCUMENTS

| | | |
|---|---|---|
| EP | 2072012 A1 | 6/2009 |
| EP | 2380496 A1 | 10/2011 |
| WO | 2013164368 A1 | 11/2013 |

OTHER PUBLICATIONS

Binder, N. et al., "The Surgeon's Third Hand an Interactive Robotic C-Arm Fluoroscope", Mobile Robotics-Moving Intelligence (2007): 403-418.

(Continued)

*Primary Examiner* — Courtney Thomas
(74) *Attorney, Agent, or Firm* — Oyen Wiggs Green & Mutala LLP

(57) ABSTRACT

An imaging system such as a medical C-arm x-ray fluoroscopy machine includes a tracking system that tracks a position of an x-ray source and an x-ray detector using sensors which monitor positions of joints which allow relative motions of segments in a support for the x-ray source and detector. Sensor readings are used in a kinematic chain. One or more segments that behave in a non-rigid manner are replaced by a virtual rigid link in the kinematic chain that takes into account deformations of the segments (e.g. under the influence of gravity). Calibration methods permit calibration of the system using images of phantoms.

22 Claims, 16 Drawing Sheets

(56) References Cited

U.S. PATENT DOCUMENTS

| | | |
|---|---|---|
| 6,491,429 B1 | 12/2002 | Suhm |
| 6,659,642 B2 | 12/2003 | Hanover |
| 6,811,313 B2 | 11/2004 | Graumann et al. |
| 7,621,169 B2 | 11/2009 | Li et al. |
| 7,697,972 B2 | 4/2010 | Verard et al. |
| 8,022,990 B2 | 9/2011 | Li et al. |
| 8,104,957 B2 | 1/2012 | Maier et al. |
| 8,350,914 B2 | 1/2013 | Li et al. |
| 8,374,678 B2 | 2/2013 | Graumann |
| 8,467,851 B2 | 6/2013 | Mire et al. |
| 8,526,700 B2 | 9/2013 | Isaacs |
| 8,792,704 B2 | 7/2014 | Isaacs |
| 2001/0053204 A1 | 12/2001 | Navab et al. |
| 2003/0060703 A1 | 3/2003 | Barrick |
| 2003/0219102 A1* | 11/2003 | Mitschke ............... A61B 6/584 378/207 |
| 2004/0171924 A1 | 9/2004 | Mire et al. |
| 2008/0039867 A1 | 2/2008 | Feussner et al. |
| 2011/0164721 A1 | 7/2011 | Jank et al. |
| 2011/0311030 A1 | 12/2011 | Grzeda et al. |
| 2011/0313285 A1 | 12/2011 | Fallavollita et al. |
| 2012/0236999 A1 | 9/2012 | Altvater et al. |
| 2012/0289821 A1 | 11/2012 | Graumann et al. |
| 2014/0114173 A1 | 4/2014 | Bar-Tal et al. |

OTHER PUBLICATIONS

Cho, Y, et al., "Accurate Technique For Complete Geometric Calibration Of Cone-Beam Computed Tomography Systems", Medical Physics 32 (4):968-983, 2005.

Daly, M.J. et al., "Geometric Calibration Of A Mobile C-Arm For Intraoperative Cone-Beam CT", Medical Physics 35 (5):2124-2136, 2008.

Binder, N. et al., "A robotic C-arm fluoroscope", The International Journal of Medical Robotics and Computer Assisted Surgery 1, No. 3 (2005): 108-116.

Jain, A. et al., "C-arm Tracking and Reconstruction Without an External Tracker", Medical Image Computing and Computer-Assisted Intervention-MICCAI 2006, pp. 494-502. Springer Berlin Heidelberg, 2006.

Matthaus, L. et al., "Closed-form inverse kinematic solution for fluoroscopic C-arms", Advanced Robotics 21, No. 8 (2007): 869-886.

Matthews, F. et al., "Navigating the Fluoroscope's C-Arm Back into Position: An Accurate and Practicable Solution to Cut Radiation and Optimize Intraoperative Workflow", Journal of Orthopaedic Trauma 21, No. 10 (2007): 687-692.

Navab, N. et al., "Visual Servoing for Intraoperative Positioning and Repositioning of Mobile C-arms", Medical Image Computing and Computer-Assisted Intervention-MICCAI 2006, pp. 551-560. Springer Berlin Heidelberg, 2006.

Wang, L. et al., "Closed-Form Inverse Kinematics for Intraoperative mobile C-arm positioning with six degrees of freedom", SPIE, vol. 7964, No. 1, p. 79641A. 2011.

Amiri, S. et al., "A Novel Multi-Planar Radiography Method for Three Dimensional Pose Reconstruction of the Patellofemoral and Tibiofemoral Joints after Arthroplasty", J. Biomech. 44(9):1757-1764, 2011.

Hofstetter, R. et al., "Fluoroscopy As An Imaging Means For Computer-Assisted Surgical Navigation", Computer Aided Surgery 4 (2):65-76, 1999.

Hofstetter, R. et al., "Computer-Assisted Fluoroscopy-Based Reduction of Femoral Fractures and Antetorsion Correction", Computer Aided Surgery: Official Journal Of The International Society For Computer Aided Surgery 5 (5):311-325, 2000.

Foley, K.T. et al., "Virtual Fluoroscopy: Computer-Assisted Fluoroscopic Navigation", Spine 26 (4):347-351, 2001.

Chen, X. et al., "Precise X-Ray and Video Overlay For Augmented Reality Fluoroscopy", International Journal of Computer Assisted Radiology and Surgery 8 (1):29-38, 2013.

Wang, L. et al., "Closed-Form Inverse Kinematics for Interventional C-Arm X-Ray Imaging With Six Degrees of Freedom: Modeling and Application", IEEE Transactions on Medical Imaging, vol. 31, No. 5, May 2012.

Reaungamornrat, S. et al., "An On-Board Surgical Tracking and Video Augmentation System for C-Arm Image Guidance", International Journal of Computer Assisted Radiology and Surgery 7 (5):647-665, 2012.

Reaungamornrat, S. et al., "Tracker-On-C: A Novel Tracker Configuration for Image-Guided Therapy Using a Mobile C-Arm", Computer Assisted Radiology And Surgery, Berlin, Germany:22-25, 2011.

Bo, L. et al., "Accuracy of Electromagnetic Tracking With a Prototype Field Generator in an Interventional OR Setting", Medical Physics 39 (1):399-406, 2012.

Hummel, J. et al., "Evaluation of a New Electromagnetic Tracking System Using a Standardized Assessment Protocol", Physics in Medicine and Biology 51(10):N205-210, 2006.

Grzeda, V. et al., "C-Arm Rotation Encoding With Accelerometers", International Journal of Computer Assisted Radiology and Surgery 5 (4):385-391, 2010.

Grzeda, V. et al., Rotational Encoding Of C-Arm Fluoroscope With Tilt Sensing Accelerometer. Lect Notes Comput Sc 6363:424-431, 2010.

Livyatan, H. et al., "Robust Automatic C-Arm Calibration for Fluoroscopy-Based Navigation: A Practical Approach", in: Dohi T, Kikinis R (Eds) Medical Image Computing and Computer-Assisted Intervention-MICCAI 2002, vol. 2489, Lecture Notes in Computer Science, Springer Berlin Heidelberg, pp. 60-68.

Burkhardt, D. et al., "A Cheap and Easy Method for 3d C-Arm Reconstruction Using Elliptic Curves", Proc Spie 6509, 2007.

Dehghan, E. et al., "Brachytherapy Seed Reconstruction With Joint-Encoded C-Arm Single-Axis Rotation and Motion Compensation", Medical Image Analysis 15 (5):760-771, 2011.

Amiri, S. et al., "A low-cost tracked C-arm (TC-arm) upgrade system for versatile quantitative intraoperative imaging", International Journal of Computer Assisted Radiology and Surgery (JCARS), available on-line Oct. 22, 2013.

* cited by examiner

TRACKING SYSTEM FOR IMAGING MACHINES AND RELATED APPARATUS

CROSS-REFERENCE TO RELATED APPLICATIONS

This application is a continuation of U.S. application Ser. No. 15/028,100, which is a 371 of International Application No. PCT/CA2014/050986 filed 10 Oct. 2014, which claims priority from U.S. Application No. 61/889,473 filed 10 Oct. 2013. For purposes of the United States, this application claims the benefit under 35 U.S.C. § 119 of U.S. Application No. 61/889,473 filed 10 Oct. 2013 and entitled SENSOR BASED TRACKED C ARM FOR QUANTITATIVE INTRAOPERATIVE ASSESSMENTS which is hereby incorporated herein by reference for all purposes.

FIELD

This invention relates to imaging and has particular but non-exclusive application to medical imaging. Embodiments of the invention provide apparatus which includes an imaging head that is movable relative to an object to be imaged (e.g. a patient) and a tracking system for monitoring positions and orientations of acquired images relative to one another and to the object being imaged. An example embodiment provides a C-arm x-ray fluoroscopy machine equipped with sensors for monitoring changes in position of an x-ray source and detector.

BACKGROUND

C-arm fluoroscopy machines are often used in hospital emergency rooms and trauma centers. These machines have an arm which supports an x-ray source spaced apart from an x-ray detector. The arm can be manipulated to place the x-ray source on one side of a patient and the x-ray detector on the other side of the patient. A series of joints permits the arm to be moved to a pose which will provide a desired x-ray image. A monitor displays the x-ray image in real time.

C-arm fluoroscopy machines may, for example, be used to image the locations at which pins or screws will be inserted to hold broken bones in place.

One issue with the use of C-arm fluoroscopy machines is limiting the amount of x-rays to which physicians and other medical personnel are exposed. In many procedures a physician's hands will be in the field irradiated by x-rays. Although modern x-ray machines can acquire acceptable images with a lower dose than was formerly possible there is a limit to the dose reduction that can be achieved by this route.

Another approach to reducing x-ray exposure to medical personnel is reducing the amount of time required to obtain desired images. Providing a mechanism to track the position of an x-ray source and detector can help to reduce the time taken to obtain desired images. A tracking system may also facilitate a range of useful functionalities that are based on known spatial positions of radiographs relative to one another and to a patient.

Optical localizers have been proposed for tracking the position of the arms of C-arm fluoroscopy machines. Such localizers use cameras to track the positions of targets mounted on the C-arm. Optical trackers have a number of deficiencies. For example, the camera requires an unobstructed line of sight to the targets. This constrains the use of valuable operating room space. This problem is made worse because a C-arm is relatively large and must be able to be moved through a large range of motion. Thus maintaining an unobstructed line of sight between camera and targets places serious constraints on the positioning of other operating room equipment and operating room personnel. In addition, optical localizers can have high costs.

The following references describe technology in the general field of the present invention:

Cho Y, Moseley Dj, Siewerdsen Jh, Jaffray Da (2005) Accurate Technique For Complete Geometric Calibration Of Cone-Beam Computed Tomography Systems. Medical Physics 32 (4):968-983

Daly Mj, Siewerdsen Jh, Cho Yb, Jaffray Da, Irish Jc (2008) Geometric Calibration Of A Mobile C-Arm For Intraoperative Cone-Beam Ct. Medical Physics 35 (5):2124-2136

Binder, Norbert, Christoph Bodensteiner, Lars Matthaus, Rainer Burgkart, and Achim Schweikard. The Surgeon's Third Hand an Interactive Robotic C-Arm Fluoroscope. Mobile Robotics—Moving Intelligence (2007): 403-418.

Binder, Norbert, Lars Matthaus, Rainer Burgkart, and Achim Schweikard. A robotic C-arm fluoroscope. The International Journal of Medical Robotics and Computer Assisted Surgery 1, no. 3 (2005): 108-116.

Jain, Ameet, and Gabor Fichtinger. C-arm tracking and reconstruction without an external tracker. In Medical Image Computing and Computer-Assisted Intervention—MICCAI 2006, pp. 494-502. Springer Berlin Heidelberg, 2006.

Matthäus, Lars, Norbert Binder, Christoph Bodensteiner, and Achim Schweikard. Closed-form inverse kinematic solution for fluoroscopic C-arms. Advanced Robotics 21, no. 8 (2007): 869-886.

Matthews, Felix, Dominik J. Hoigne, Manfred Weiser, Guido A. Wanner, Pietro Regazzoni, Norbert Suhm, and Peter Messmer. Navigating the fluoroscope's C-arm back into position: an accurate and practicable solution to cut radiation and optimize intraoperative workflow. Journal of orthopaedic trauma 21, no. 10 (2007): 687-692.

Navab, Nassir, Stefan Wiesner, Selim Benhimane, Ekkehard Euler, and Sandro Michael Heining. Visual servoing for intraoperative positioning and repositioning of mobile C-arms. In Medical Image Computing and Computer-Assisted Intervention—MICCAI 2006, pp. 551-560. Springer Berlin Heidelberg, 2006.

Wang, Lejing, Rui Zou, Simon Weidert, Juergen Landes, Ekkehard Euler, Darius Burschka, and Nassir Navab. Closed-form inverse kinematics for intra-operative mobile C-arm positioning with six degrees of freedom. In SPIE, vol. 7964, no. 1, p. 79641A. 2011.

Wang, Lejing, Pascal Fallavollita, Rui Zou, Xin Chen, Simon Weidert, and Nassir Navab. Closed-form inverse kinematics for interventional C-arm X-ray imaging with six degrees of freedom: modeling and application. Medical Imaging, IEEE Transactions on 31, no. 5 (2012): 1086-1099.

Hofstetter R, Slomczykowski M, Sati M, Nolte Lp (1999) Fluoroscopy As An Imaging Means For Computer-Assisted Surgical Navigation. Computer Aided Surgery 4 (2):65-76

Hofstetter R, Slomczykowski M, Krettek C, Koppen G, Sati M, Nolte Lp (2000) Computer-Assisted Fluoroscopy-Based Reduction Of Femoral Fractures And Antetorsion Correction. Computer Aided Surgery: Official Journal Of The International Society For Computer Aided Surgery 5 (5):311-325. Doi:10.1002/1097-0150(2000)5:5<311::Aid-Igs1>3.0.Co; 2-J Foley Kt, Simon Da, Rampersaud Yr (2001) Virtual Fluoroscopy: Computer-Assisted Fluoroscopic Navigation. Spine 26 (4):347-351

Chen X, Wang L, Fallavollita P, Navab N (2013) Precise X-Ray And Video Overlay For Augmented Reality Fluoroscopy. International Journal Of Computer Assisted Radiology And Surgery 8 (1):29-38. Doi:10.1007/S11548-012-0746-X Binder N, Matthaus L, Burgkart R, Schweikard A (2005) A Robotic C-Arm Fluoroscope. The International Journal Of Medical Robotics+Computer Assisted Surgery: Mrcas 1 (3):108-116. Doi:10.1002/Rcs.34

Reaungamornrat S, Otake Y, Uneri A, Schafer S, Mirota Dj, Nithiananthan S, Stayman Jw, Kleinszig G, Khanna Aj, Taylor Rh, Siewerdsen Jh (2012) An On-Board Surgical Tracking And Video Augmentation System For C-Arm Image Guidance. International Journal Of Computer Assisted Radiology And Surgery 7 (5):647-665. Doi: 10.1007/S11548-012-0682-9

Reaungamornrat S, Otake Y, Uneri A, Schafer S, Stayman J, Zbijewski W, Mirota D, Yoo J, Nithiananthan S, Khanna A (2011) Tracker-On-C: A Novel Tracker Configuration For Image-Guided Therapy Using A Mobile C-Arm. Computer Assisted Radiology And Surgery, Berlin, Germany:22-25

Bo Le, Leira Ho, Tangen Ga, Hofstad Ef, Amundsen T, Lango T (2012) Accuracy Of Electromagnetic Tracking With A Prototype Field Generator In An Interventional Or Setting. Medical Physics 39 (1):399-406. Doi:10.1118/1.3666768

Hummel J, Figl M, Birkfellner W, Bax Mr, Shahidi R, Maurer Cr, Jr., Bergmann H (2006) Evaluation Of A New Electromagnetic Tracking System Using A Standardized Assessment Protocol. Physics In Medicine And Biology 51 (10):N205-210. Doi:10.1088/0031-9155/51/10/N01

Grzeda V, Fichtinger G (2010) C-Arm Rotation Encoding With Accelerometers. International Journal Of Computer Assisted Radiology And Surgery 5 (4):385-391. Doi:Doi 10.1007/S11548-010-0415-X Grzeda V, Fichtinger G (2010) Rotational Encoding Of C-Arm Fluoroscope With Tilt Sensing Accelerometer. Lect Notes Comput Sc 6363:424-431

Livyatan H, Yaniv Z, Joskowicz L (2002) Robust Automatic C-Arm Calibration For Fluoroscopy-Based Navigation: A Practical Approach. In: Dohi T, Kikinis R (Eds) Medical Image Computing And Computer-Assisted Intervention—Miccai 2002, Vol 2489. Lecture Notes In Computer Science. Springer Berlin Heidelberg, Pp 60-68. Doi: 10.1007/3-540-45787-9_8

Burkhardt D, Jain A, Fichtinger G (2007) A Cheap And Easy Method For 3d C-Arm Reconstruction Using Elliptic Curves. Proc Spie 6509. Doi:Artn 65090b. Doi: 10.1117/12.712395

Dehghan E, Jain Ak, Moradi M, Wen X, Morris Wj, Salcudean Se, Gichtinger G (2011) Brachytherapy Seed Reconstruction With Joint-Encoded C-Arm Single-Axis Rotation And Motion Compensation. Medical Image Analysis 15 (5):760-771. Doi: 10.1016/J.Media.2011.05.017

U.S. Pat. No. 6,285,902B1: COMPUTER ASSISTED TARGETING DEVICE FOR USE IN ORTHOPAEDIC SURGERY

U.S. Pat. No. 7,621,169B2: SYSTEMS AND METHODS FOR INTEGRATING A NAVIGATION FIELD REPLACEABLE UNIT INTO A FLUOROSCOPY SYSTEM

U.S. Pat. No. 8,022,990B2: SYSTEMS AND METHODS FOR ON-LINE MARKER-LESS CAMERA CALIBRATION USING A POSITION TRACKING SYSTEM

U.S. Pat. No. 8,467,851B2: METHOD AND APPARATUS FOR POSITIONING A REFERENCE FRAME

U.S. Pat. No. 8,526,700B2: IMAGING SYSTEM AND METHOD FOR SURGICAL AND INTERVENTIONAL MEDICAL PROCEDURES

U.S. Pat. No. 8,792,704B2: IMAGING SYSTEM AND METHOD FOR USE IN SURGICAL AND INTERVENTIONAL MEDICAL PROCEDURES

W2013164368A1: IMAGE DISTORTION CORRECTION AND ROBUST PHANTOM DETECTION

EP2072012A1: Method for calibration of a camera augmented C-arm

U.S. Pat. No. 6,049,582: C-ARM CALIBRATION METHOD FOR 3D RECONSTRUCTION

U.S. Pat. No. 6,200,024: VIRTUAL C-ARM ROBOTIC POSITIONING SYSTEM FOR USE IN RADIOGRAPHIC IMAGING EQUIPMENT

U.S. Pat. No. 6,477,400B1: FLUOROSCOIC IMAGE GUIDED ORTHOPAEDIC SURGERY WITH INTRAOPERATIVE REGISTRATION

U.S. Pat. No. 6,491,429: METHOD OF AUTOMATIC GUIDING A C-ARM X-RAY DEVICE

U.S. Pat. No. 6,659,642: NON-CIRCULAR C-ARM FOR FLUOROSCOPIC IMAGING EQUIPMENT

U.S. Pat. No. 6,811,313: C-ARM X-RAY SYSTEM WITH ADJUSTABLE DETECTOR POSITIONING

U.S. Pat. No. 8,104,957: CALIBRATING AC-ARM X-RAY APPARATUS

U.S. Pat. No. 8,374,678: MEDICAL APPARATUS WITH IMAGE ACQUISITION DEVICE AND POSITION DETERMINATION DEVICE COMBINED IN THE MEDICAL APPARATUS

US2001/0053204A1: METHOD AND APPARATUS FOR RELATIVE CALIBRATION OF A MOBILE X-RAY C-ARM AND AN EXTERNAL POSE TRACKING SYSTEM

US2003/0060703A1: FLUOROSCOPIC IMAGE GUIDED ORTHOPAEDIC SURGERY SYSTEM WITH INTRAOPERATIVE REGISTRATION

US2004/0171924A1: METHOD AND APPARATUS FOR PREPLANNING A SURGICAL PROCEDURE

US2011/0164721A1: X-RAY IMAGE RECORDING SYSTEM AND X-RAY RECORDING METHOD FOR RECORDING IMAGE DATA WITH X-RAY UNITS FOR VOLUME RECONSTRUCTION

US2011/0311030A1: C-ARM ROTATION ENCODING METHODS AND APPARATUS

US2012/0289821A1: C-ARM INTEGRATED ELECTROMAGNETIC TRACKING SYSTEM

There remains a need for practical and cost-effective ways to accurately track the positions of imaging devices such as C-arm x-ray fluoroscopy machines.

SUMMARY

This invention has a number of aspects. These include: imaging systems which include tracking systems, tracking systems useful with imaging systems, methods for tracking imaging systems and methods for calibrating tracking systems.

Preferred embodiments include sensors that monitor positions of individual joints of an imaging system such as, for example, a C-arm x-ray fluoroscopy machine. These sensors may be built into the machine when it is manufactured, added on, or retrofitted to an existing machine. Positions of imaging components (e.g. the x-ray source and detector) may then be tracked by treating the body construct of the imaging machine as a kinematic chain and following the sequential movements of multiple joints of the machine (as determined by the sensors) from the base to the holder of the image detector. In some embodiments the image detector comprises two parts and both parts may be tracked. For example, an x-ray source and an x-ray detector may both be tracked by following joints along kinematic chains extending from the base to both parts of the image detector. A main challenge is that the joints and structural parts of an imaging machine are in general not rigid. This is especially true for the C-frames of typical C-arm imaging machines. The C-frames are large structures which tend to bend and twist under the gravitational forces. C-frames have parts that project generally horizontally. These parts can sag under the influence of gravity like cantilever beams. The nature of the bending and twisting can change depending on the imaging angle.

A method for calibration of a C-arm fluoroscope when the holder of the C-arm is tracked by any type of one or more degree of freedom (DOF) mechanical/electrical motion tracking encoders involves modelling the body structure of a C-arm as a kinematic chain in which a number of non-rigid components of the C-arm fluoroscope, most typically the C-frame and one or more segments connecting the C-frame to a generally rigid part of the body structure, are replaced by a virtual rigid link between an origin or other reference point in the imaging space and the last rigid body segment in the kinematic chain. This treatment eliminates the non-rigid bodies from the kinematic chain and permits rigid body tracking of the rest of the body segments of the C-arm machine, while permitting compensation for deformations of the flexible links (e.g. due to gravity). An example method involves steps of:

acquiring images at various orbit and tilt angles of the C-frame of a calibration phantom (which will be referred to herein as a Gantry Calibration Phantom or "GCP") fixed within the imaging field of view of the device, and measuring the corresponding orbit and tilt angles of the C-frame (using any of various possible methods including rotational encoders);

calibrating individual joints of the device using a phantom (referred to in this disclosure as a Slab Calibration Phantom or "SCP") that has a particular pattern of features (e.g. radio-opaque markers) at known locations that can be uniquely identified in radiographic projection images of the SCP. An example SCP has small markers such as ball bearings that are held at accurately pre-defined positions. Sizes of the markers vary in a known pattern such that a radiographic projection showing a few of the markers allows the markers in the radiographic projection to be uniquely identified with exact coordinates in a frame of reference of the SCP. The SCP may be placed stationary in the field of view of the C-arm machine. Image analysis of oblique bi-planar views of the SCP permit reconstruction of the SCP with respect to a fixed coordinate system in the imaging space. For calibration, each joint of the device can be moved individually and the phantom will be reconstructed before and after each motion. The calibration information generated for each joint (which may, for example include the vector direction of the axis of each joint with respect to a common imaging frame of reference, a scaling coefficient for sensor output values and a zeroing offset value) is stored for later use;

optionally, motion of the entire C-arm device may be tracked. For example, the base of the C-arm device may include a carriage which can be unlocked so that the base can be moved. For example, motions of a carriage of the C-arm device may be tracked individually with respect to a fixed reference using a localizer or by other means. Tracking of the motion of the carriage may be calibrated using a SCP. For example, such calibration may involve moving the carriage to various positions, acquiring sequential bi-planar images of the SCP at the different positions, reconstructing the portion of the SCP that is visible in the images and calculating a homogenous transformation between the coordinates of the tracker and the imaging coordinate system. If position information from the carriage is calibrated, the carriage may be included as a link in the kinematic chain (where the length and vector direction of the link are determined based on the coordinates of the tracker being applied to track motions of the base relative to the fixed reference.

The acquired calibration data can subsequently be used along with live readings from individual sensors that monitor various joints of the kinematic chain to produce live tracking of the x-ray source and detector based on the prescribed kinematic model.

Assuming that the SCP can be laid flat on a horizontal surface within the field of view, if the direction of imaging is placed at +/−45 degrees with respect to a vertical line, this provides near to orthogonal bi-planar image views for most accurate reconstruction of the SCP. The sizes and arrangements of the features in the SCP allow for automatic detection of the position of features in radiographic images of the SCP and subsequently automatic reconstruction of the SCP in three-dimensions based on the stereo radiographic views with respect to the imaging coordinate system. In some embodiments a single phantom may include features that allow the phantom to be used both as a SCP and as a GCP.

An advantage of certain embodiments is that there is no need for a highly accurate localizer for calibrating the C-arm or for intra-operative use. The calibration allows kinematic tracking of the C-arm based on a kinematic chain while the non-idealistic bending and torsion of the structure under gravitational forces can be accounted for.

In some embodiments tracking is achieved to a positional accuracy better than +/−4 mm. In some embodiments positional accuracy better than +/−2 mm may be achieved.

The following are a few non-limiting representative example enumerated embodiments of the invention:

1. A medical imaging apparatus comprising:

a support operable to hold an imaging head at a desired position relative to a patient, the support comprising a base and three or more segments connected to one another by adjustable joints such that a first one of the segments is coupled to the base by a first one of the adjustable joints and the imaging head is supported on a last one of the segments and is movable in space by adjusting the adjustable joints;

a plurality of sensors, the plurality of sensors operative to monitor configurations of each of the adjustable joints;

a data processor connected to receive outputs from the plurality of sensors and to estimate a current position of the imaging head by:

treating a first set of the segments comprising a first plurality of the segments and the adjustable joints between them as a first part of a kinematic chain, the first part of the kinematic chain extending from the base to an end of the first part of the kinematic chain, the first part of the kinematic chain excluding a second set of the segments comprising one or more second segments including the last segment and determining a position of the end of the first part of the kinematic chain relative to the base based on geometries of the first plurality of the segments and configurations of the adjustable joints included in the first part of the kinematic chain, the configurations of the adjustable joints included in the first part of the kinematic chain determined from the outputs of the sensors;

determining from the output signals of the sensors a configuration of each of the one or more of the adjustable joints located between the end of the first part of the kinematic chain and the last segment and based on the determined configurations of the one or more of the adjustable joints located between the end of the first part of the kinematic chain and the last segment looking up first calibration coordinates indicative of a vector displacement of the imaging head relative to a point having a predetermined location relative to the end of the first part of the kinematic chain; and based on the first calibration coordinates extending the kinematic chain from the end of the first part of the kinematic chain to the imaging head.

2. Imaging apparatus according to aspect 1 or any other disclosed aspect wherein the calibration coordinates include coordinates indicating an orientation of the imaging head in space corresponding to the determined configuration of the one or more of the adjustable joints located between the end of the first part of the kinematic chain and the last segment.

3. Imaging apparatus according to aspect 1 or aspect 2 or any other disclosed aspect wherein the adjustable joints located between the end of the first part of the kinematic chain and the last segment include a joint controlling a tilt angle of the last segment.

4. Imaging apparatus according to any one of aspects 1 to 3 or any other disclosed aspect wherein the adjustable joints located between the end of the first part of the kinematic chain and the last segment include a joint controlling an orbit angle of the last segment.

5. Imaging apparatus according to any one of aspects 1 to 4 or any other disclosed aspect wherein the calibration coordinates take into account gravitational distortion of the last segment.

6. Imaging apparatus any one of aspects 1 to 4 wherein the calibration coordinates take into account gravitational distortion of the portion of the support between the end of the first part of the kinematic chain and the imaging head.

7. Imaging apparatus according to any one of aspects 1 to 6 or any other disclosed aspect wherein the calibration coordinates are coordinates in a coordinate system associated with a frame of reference that is fixed relative to the end of the first part of the kinematic chain.

8. Imaging apparatus according to aspect 7 or any other disclosed aspect wherein extending the kinematic chain from the end of he first part of the kinematic chain to the imaging head comprises including in the kinematic chain a rigid virtual link extending from the end of the first part of the kinematic chain to a reference point in a coordinate system associated with the frame of reference.

9. Imaging apparatus according to aspect 8 wherein the imaging head comprises an x-ray detector, the imaging apparatus comprises an x-ray source and the reference point is between the x-ray source and the x-ray detector.

10. Imaging apparatus according to aspect 8 or any other disclosed aspect wherein the adjustable joints located between the end of the first part of the kinematic chain and the last segment include a plurality of the adjustable joints and the processor is configured to determine parameters of the virtual link based on a configuration of a first one of the adjustable joints.

11. Imaging apparatus according to any one of aspects 1 to 8 or any other disclosed aspect wherein the imaging head comprises an x-ray detector.

12. Imaging apparatus according to aspect 11 or any other disclosed aspect wherein the x-ray detector and an x-ray source are mounted on the last segment in spaced-apart relationship to one another.

13. Imaging apparatus according to aspect 12 or any other disclosed aspect wherein the data processor is configured to look up second calibration coordinates based on the determined configurations of the one or more of the adjustable joints located between the end of the first part of the kinematic chain and the last segment wherein the first calibration coordinates are indicative of a location of the x-ray detector relative to the point and the second calibration coordinates are indicative of a location of the x-ray source relative to the point.

14. Imaging apparatus according to any one of aspects 1 to 13 wherein the last segment comprises a C-frame and the adjustable joints between the C-frame and the end of the kinematic chain permit only orbit and tilt motions of the C-frame.

15. Imaging apparatus according to aspect 14 or any other disclosed aspect wherein the sensors include a first inertial sensor mounted to the C-frame and the data processor is configured to determine orbit and tilt angles of the C-frame based on outputs of the first inertial sensor.

16. Imaging apparatus according to any one of aspects 1 to 15 or any other disclosed aspect wherein the adjustable joints included in the first part of the kinematic chain include a first joint adjustable to move the end of the kinematic chain vertically, a second joint adjustable to move the end of the kinematic chain horizontally and a third joint adjustable to rotate the end of the kinematic chain about a vertical axis.

17. Imaging apparatus according to any one of aspects 1 to 16 or any other disclosed aspect wherein the base comprises a movable carriage, the apparatus comprises a tracking system operative to monitor positions of the base relative to a fixed frame of reference and the processor is configured to determine the position of the imaging head relative to the fixed frame of reference.

18. Imaging apparatus according to any one of aspects 1 to 17 or any other disclosed aspect wherein looking up the first calibration coordinates comprises interpolating between a plurality of values associated with the determined configurations of the one or more of the adjustable joints located between the end of the first part of the kinematic chain and the last segment.

19. Imaging apparatus according to any one of aspects 1 to 18 or any other disclosed aspect wherein the imaging head is operable to generate image data and the data processor is configured to associate with image data representing an image data indicating a position of the imaging head when the image was acquired.

20. Imaging apparatus according to any one of aspects 1 to 19 or any other disclosed aspect comprising a display wherein the data processor is configured to display on the display a current position of the imaging head.

21. Imaging apparatus according to any one of aspects 1 to 20 or any other disclosed aspect wherein the adjustable joints located between the end of the first part of the kinematic chain and the last segment include a plurality of the adjustable joints and looking up the first calibration coordinates comprising, based on a configuration of a first one of the adjustable joints selecting one of a plurality of lookup tables and looking up the first calibration coordinates in the selected lookup table.

22. A method for tracking position of an imaging head in an imaging machine comprising a support comprising a base and three or more segments connected to one another by adjustable joints such that a first one of the segments is coupled to the base by a first one of the adjustable joints and the imaging head is supported on a last one of the segments and is movable in space by adjusting the adjustable joints, the method comprising:
determining configurations of the adjustable joints;
modelling a first set of the segments comprising a first plurality of the segments and the adjustable joints between them as a first part of a kinematic chain extending from the base to an end of the first part of the kinematic chain;
based on the configurations of one or more of the adjustable joints located between the end of the first part of the kinematic chain and the last segment looking up first calibration coordinates indicative of a vector displacement of the imaging head relative to a point having a predetermined location relative to the end of the first part of the kinematic chain; and
based on the first calibration coordinates extending the kinematic chain from the end of the first part of the kinematic chain to the imaging head.

23. A method according to aspect 22 or any other disclosed aspect wherein the imaging head comprises an x-ray source and an x-ray detector, the first displacement vector indicates a position of the x-ray source relative to the end of the kinematic chain and the method further includes based on the configurations of one or more of the adjustable joints located between the end of the first part of the kinematic chain and the last segment looking up second calibration coordinates indicative of a position of the x-ray detector relative to the end of the first part of the kinematic chain.

14. A method according to aspect 22 or 23 or any other disclosed aspect wherein the last segment comprises a C-frame and the first calibration coordinates take into account gravitationally-induced distortions of the C-frame.

25. A method according to any one of aspects 22 to 25 or any other disclosed aspect comprising generating the first calibration coordinates by processing images of a phantom obtained using the imaging head at different configurations of the adjustable joints located between the end of the first part of the kinematic chain and the last segment.

26. A method according to any one of aspects 22 to 25 or any other disclosed aspect wherein the last segment comprises a C-frame and the adjustable joints between the C-frame and the end of the kinematic chain permit only orbit and tilt motions of the C-frame.

27. A method according to aspect 26 or any other disclosed aspect comprising determining angles of orbit and tilt of the C-frame by processing an output signal from an inertial sensor attached to the C-frame.

28. A method according to any one of aspects 22 to 27 or any other disclosed aspect wherein the base comprises a movable carriage and the method comprises tracking a position of the base relative to a fixed frame of reference.

29. A method according to any one of aspects 22 to 28 or any other disclosed aspect wherein looking up the first calibration coordinates comprises interpolating between a plurality of values associated with the determined configurations of the one or more of the adjustable joints located between the end of the kinematic chain and the last segment.

30. A method according to any one of aspects 22 to 29 or any other disclosed aspect comprising acquiring image data comprising images with the imaging head and associating with the image data for one of the images data indicating a position of the imaging head when the image was acquired.

31. A method according to any one of aspects 22 to 30 or any other disclosed aspect comprising displaying on a display a current position of the imaging head.

32. A method according to any one of aspects 22 to 31 or any other disclosed aspect wherein the adjustable joints included in the kinematic chain include a first joint adjustable to move the end of the kinematic chain vertically and a second joint adjustable to move the end of the kinematic chain horizontally and the method comprises monitoring configurations of the first and second joints using non-contact distance sensors.

33. A method according to aspect 32 or any other disclosed aspect wherein the adjustable joints included in the kinematic chain include a third joint adjustable to rotate the end of the kinematic chain about a vertical axis and the method comprises determining a wig-wag angle of the third joint by processing an output of an inertial sensor attached to a segment of the support toward the end of the kinematic chain from the third joint.

33. A method according to any one of aspects 22 to 31 or any other disclosed aspect wherein the adjustable joints included in the kinematic chain include a rotational joint adjustable to rotate the end of the kinematic chain about a vertical axis and the method comprises determining a wig-wag angle of the rotational joint by processing an output of an inertial sensor attached to a segment of the support toward the end of the kinematic chain from the rotational joint.

34. Apparatus for tracking the location of an imaging head in an imaging machine, the apparatus comprising:
a plurality of sensors, the plurality of sensors operative to monitor configurations of adjustable joints in a support structure of the imaging machine;
a data processor connectable to receive outputs from the plurality of sensors and to estimate a current position of the imaging head by:
treating a first set of the segments comprising a first plurality of the segments and the adjustable joints between them as a first part of a kinematic chain, the first part of the kinematic chain extending from the base to an end of the first part of the kinematic chain, the first part of the kinematic chain excluding a second set of the segments comprising one or more second segments including the last segment and determining a position of the end of the first part of the kinematic chain relative to the base based on geometries of the first plurality of the segments and configurations of the adjustable joints included in the first part of the kinematic chain, the configurations of the adjustable joints included in the first part of the kinematic chain determined from the outputs of the sensors;
determining from the output signals of the sensors a configuration of each of the one or more of the adjustable joints located between the end of the first part of the kinematic chain and the last segment and based on the determined configurations of the one or more of the adjustable joints located between the end of the first part of the kinematic chain and the last segment looking up first calibration coordinates indicative of a vector displacement of the imaging head relative to a point having a predetermined location relative to the end of the first part of the kinematic chain; and based on the first calibration coordinates extending the kinematic chain from the end of the first part of the kinematic chain to the imaging head.

35. Apparatus according to aspect 34 or any other disclosed aspect wherein the plurality of sensors includes first and second non-contact linear position sensors mounted at right angles to one another.
36. Apparatus according to aspect 35 or any other disclosed aspect wherein the non-contact linear position sensors comprise laser distance sensors.
37. Apparatus according to any one of aspects 34 to 36 or any other disclosed aspect wherein the plurality of sensors comprises a three-axis inclination sensor.
38. Apparatus according to any one of aspects 34 to 36 or any other disclosed aspect wherein the plurality of sensors comprises an inertial rotation sensor.
39. Apparatus according to aspect 38 or any other disclosed aspect comprising a wireless data interface connecting the inertial rotation sensor to the data processor.
40. A method for determining a relationship between motions of an adjustable joint in a support for an imaging head and an image coordinate system, the method comprising:

with the adjustable joint at a first position acquiring a first set of one or more images of a slab calibration phantom comprising features identifiable with position on the slab calibration phantom and acquiring a first sensor value output by a sensor monitoring the adjustable joint;

with the adjustable joint at a second position different from the first position acquiring a second set of one or more images of the slab calibration phantom and acquiring a second sensor value output by the sensor monitoring the adjustable joint;

processing each of the first and second sets of images to identify a plurality of features of the slab calibration phantom present in the corresponding set of images;

based on positions of the identified features in the images of the sets of images determining first and second positions on the slab calibration phantom corresponding to the first and second positions of the adjustable joint in the image frame of reference; and, based on a known spatial relationship among the features of the slab calibration phantom and the first and second positions determining a vector in the image frame of reference representing a direction and magnitude of the displacement of the imaging head between the first and second positions of the adjustable joint determining a scale factor between the values output by the sensor and the displacement resulting from adjustment of the adjustable joint.

41. A method according to aspect 40 or any other disclosed aspect wherein the adjustable joint is a linear translation joint.
42. A method according to aspect 40 or any other disclosed aspect wherein the adjustable joint is a rotational joint, the method comprises: with the adjustable joint at a third position different from the first and second positions, acquiring a third set of one or more images of the slab calibration phantom and acquiring a third sensor value output by the sensor monitoring the adjustable joint;

processing the third sets of images to identify a plurality of features of the slab calibration phantom present in the third set of images; and based on positions of the identified features in the images of the first, second and third sets of images determining a location and orientation of an axis of rotation of the adjustable joint.

43. Apparatus having any new and inventive feature, combination of features, or sub-combination of features as described herein.
44. Methods having any new and inventive steps, acts, combination of steps and/or acts or sub-combination of steps and/or acts as described herein.

Further aspects of the invention and features of example embodiments of the invention are described in the following description, in the disclosure and/or drawings of priority application No. U.S. 61/889,473 filed 10 Oct. 2013 which is hereby incorporated herein by reference and/or illustrated in the accompanying drawings.

BRIEF DESCRIPTION OF THE DRAWINGS

The accompanying drawings illustrate non-limiting example embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
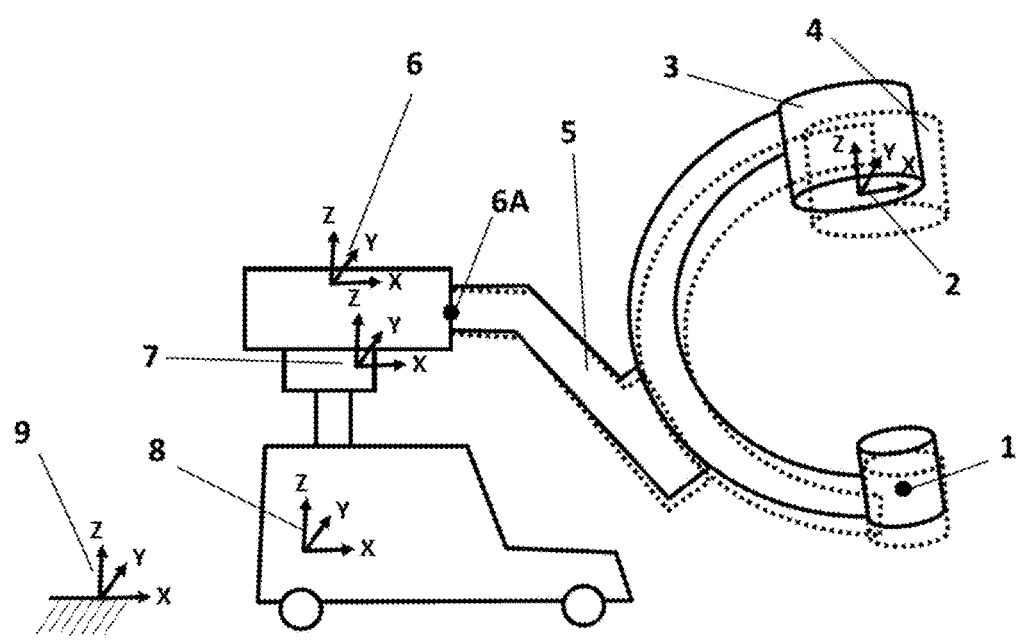
FIG. 1 is a schematic elevation view of an example C-frame x-ray machine in which and x-ray source and detector are supported by a support comprising a C-frame and a number of body segments arranged in a chain linked by joints which permit relative motions of the segments.

FIG. 1 shows an example C-arm x-ray apparatus comprising a C shape frame 3 that holds an x-ray source 1 near one end and an image detector 2 near another end. C-frame 3 is connected to a carriage 8 through a series of connected segments (5, 6, 7) and joints (32, 34, 36) (illustrated in FIG. 3) that allow C-frame 3 to be placed at different positions and orientations with respect to a patient. Assuming that the segments of a C-arm device are highly rigid, by knowing the geometry of the joints and segments and the motion undergone at the individual joints between the segments of the C-arm device, the position of C-frame 3 with respect to the carriage 8 can be predicted. If the position of carriage 8 is also known (for example if some tracking means is provided to monitor the position and orientation of carriage 8) then the positions of the individual joints can be used to determine the positions of C-frame 3 and x-ray source 1 and image detector 2 with respect to a reference frame 9 fixed in space. In the illustrated embodiment, a control unit 28 (shown in FIG. 3) comprising a data processor is connected to receive inputs from encoders or other sensors that monitor positions of joints (32, 34, 36) and to calculate the positions of x-ray source 1 and image detector 2 (or equivalently a plane and location of the current image) from those sensor readings.

Segments of a typical C-arm x-ray fluoroscopy machine are sufficiently non-rigid that they will deflect enough under load (as shown by 4 in FIG. 1) to introduce a significant deviation between the actual position of C-frame 3 and the position calculated on the assumption that all of the segments are perfectly rigid. The cantilever arrangement of C-frame 3 and its holder 5 tends to make deflections of these parts particularly significant under the effects of gravitational forces. In the typical case where deflections can be significant, control unit 28 is configured to compensate for those deflections.

A method for accounting for deflections according to some preferred embodiments treats a first part of the supporting structure which is rigid enough that it can be assumed to behave as a rigid body or set of linked rigid bodies separately from a second part of the support structure that exhibits larger deviations from rigidity. For example, the first part of the support structure may include carriage 8, segment 6 and any intervening segments. The first part of the support structure may be modeled as a kinematic chain (using sensor signals indicating positions of joints in the first part of the supporting structure and known geometries of segments of the first part of the supporting structure. For example, in the illustrated embodiment, such a kinematic chain model may be applied to predict the location and orientation of point 6A of segment 6 to which the rest of the supporting structure (e.g. C-frame 3 and any intermediate segments) is attached with acceptable accuracy.

The segments and/or joints that second part of the support structure may be distorted in different ways (e.g. under the effects of gravity). These distortions may depend upon the configurations of joints in the second part of the support structure (e.g. tilt and orbit angles for a C-frame). The method uses the joint configuration of the second part to look up calibration information that indicates the position of an imaging head relative to the point where the second part of the support structure connects to the first part of the support structure. The calibration information may be based on actual measurements of the position of the imaging head for different configurations of the joints of the second part of the support structure. The configurations of these joints (e.g. tilt and orbit angles) may be obtained by taking sensor readings.

For an X-ray machine, calibration information may, for example, comprise information specifying the position and orientation of an x-ray detector and the position of an x-ray source in a coordinate system in which the location and orientation of the point at which the first and second parts of the supporting structure connect together (e.g. the end 6A of segment 6) is also known. This calibration may be specified in a wide range of ways. In some embodiments the position of an imaging head is specified by a virtual link 13 in the kinematic chain that extends in a known distance and orientation from the point at which the first and second parts of the support structure connect and coordinates of the imaging head (e.g. an x-ray detector and/or source) in a coordinate space fixed relative to the virtual link. The coordinates may be relative to a reference point at an end of the virtual link.

Figure 2:
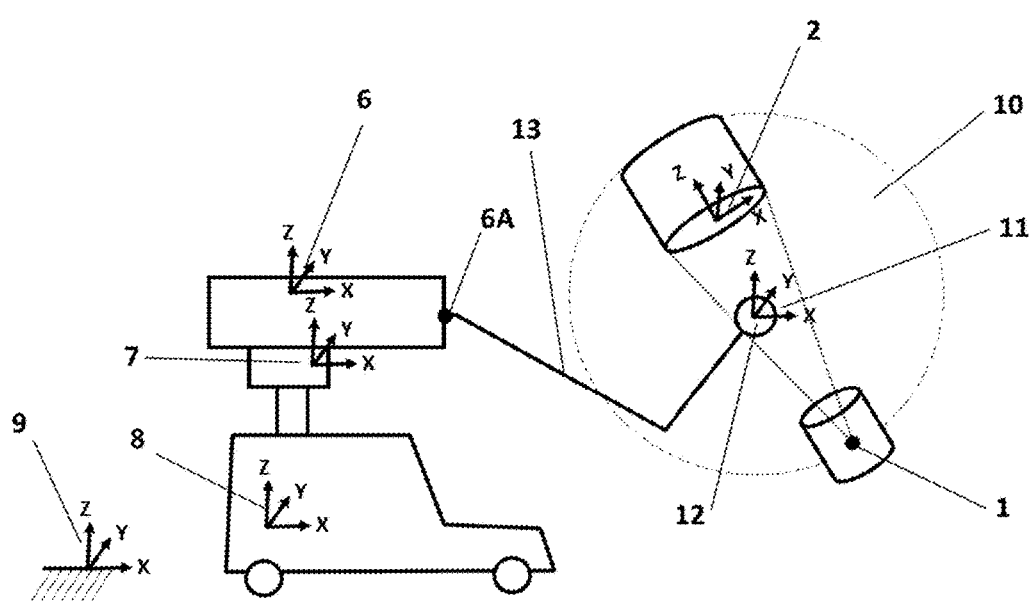
FIG. 2 is a schematic illustration showing a kinematic model of the machine shown in FIG. 1 which includes a virtual link that stands in for one or more deformable segments in the machine.

An example embodiment can be best understood by considering a model of the x-ray machine in which the 'flexible' segments (in this example C-frame 3 and segment 5) are replaced by a virtual non-deformable link 13 (see FIG. 2). One end of the virtual link is rigidly connected to a part of the supporting structure which can be assumed to behave as a rigid body or set of linked rigid bodies (in this case the connection is at end 6A of segment 6). The other end of virtual link 13 is rigidly connect to a coordinate frame 11 which stays stationary as C-frame 3 orbits and tilts through movements of C-frame 3 and/or segment 5. "Orbit" means rotation of the C-frame in the plane of the C structure. "Tilt" means rotation about a horizontal axis. When applied to a C-frame tilt means rotation of the C-frame about a horizontal axis perpendicular to the axis of "orbit".

With this model, gravity-induced deformations of C-frame 3 and segment 5 can be viewed as changes in position of source 1 and detector 2 in a coordinate space 10 attached to reference frame 11 as a function of tilts and orbits of C-frame 3.

A calibration may be performed in two stages. One stage accurately determines the positions of x-ray source 1 and image detector 2 in coordinate space 10 with respect to reference frame 11 for a given tilt and orbit of C-frame 3. This may be done, for example, by processing images of a GCP obtained for different tilt and orbit angles. Another calibration stage determines the motion with respect to a common imaging coordinate system that results from moving each individual joint. This calibration stage may be performed using images taken of a SCP for different positions of each joint. Once calibrations are performed rigid body forward kinematics can be used to predict the positions of x-ray source 1 and image detector 2 with respect to segment 6 and sequentially to segment 7, carriage 8 and fixed reference frame 9 by following the links of the kinematic chain (see FIGS. 2 and 3). Advantageously, such calibration can be performed without need for a separate optical system for tracking the positions of x-ray source 1 and image detector 2.

Figure 3:
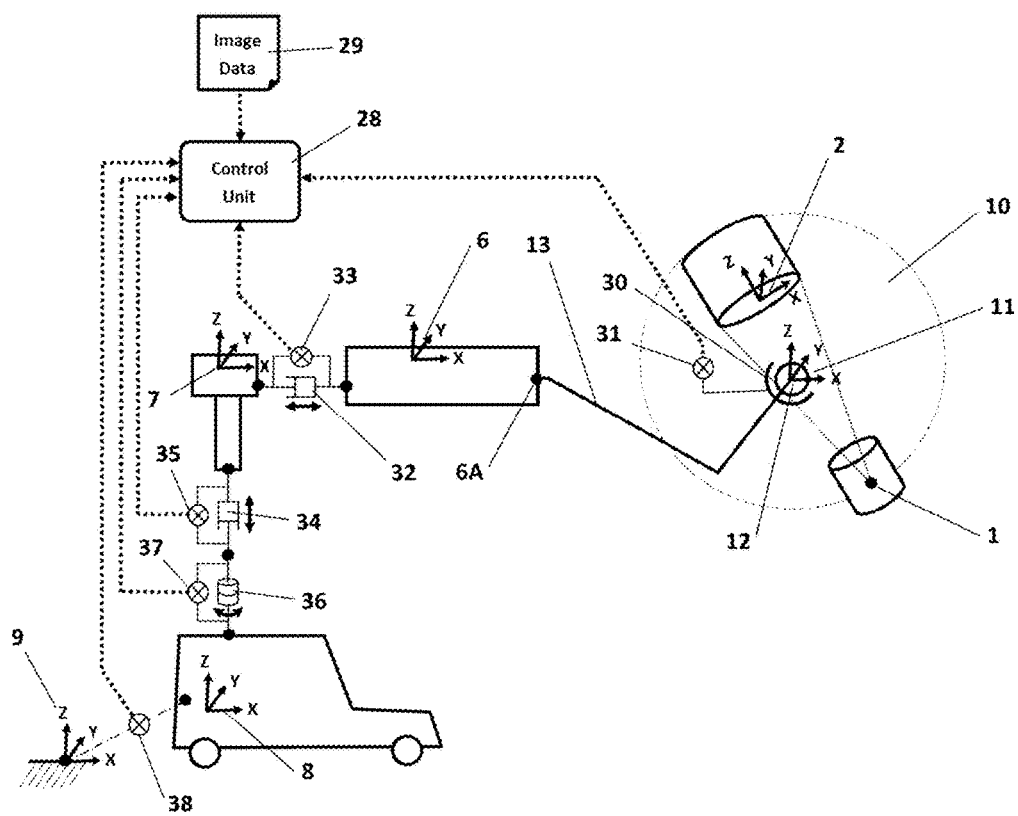
FIG. 3 is a schematic view illustrating motion of joints and a position tracking system in a non-limiting example embodiment.

For the example C-arm machine shown in FIG. 1, motion encoders can be mounted at the joints between segments of the C-arm machine during manufacturing or as an add-on option to provide kinematic tracking of the rigid segments as shown in FIG. 3. In the example embodiment shown in FIG. 3, the encoders include a distance (displacement) encoder 33 mounted on joint 32 for tracking the relative position of segment 6 with respect to segment 7, a distance encoder 35 mounted on joint 34 and a rotation encoder 37 mounted on joint 36 for tracking the position of segment 7 with respect to carriage 8.

Kinematic tracking system 28 can determine the positions of x-ray source 1 and image detector 2 with respect to a fixed reference on the carriage 8 (or fixed reference 9 in case a tracking system is provided to track the position of carriage 8 relative to fixed reference 9) by using the calibration information along with readings of the sensors 33, 35, and 37 in addition to the information about the tilt and orbit of C-frame 3 within the coordinate space 10 obtained from sensor 31. The tilt and orbit angles 31 of C-frame 3 may be determined, for example by: a two-axis inclinometer or a three-axis accelerometer or an inertial sensor mounted on C-frame 3; and/or encoders connected to monitor positions of the joints that permit tilt and orbit of C-frame 3. If carriage 8 can be fixed in position (e.g. by applying brakes to its wheels) tracking the relative position between carriage 8 and fixed frame of reference 9 may be unnecessary. For applications where carriage 8 will be moved during a procedure an additional tracking link 38 may be provided between carriage 8 and fixed reference frame 9 as shown in FIG. 3.

Calibration may be performed by determining how different tilts and orbits of C-frame 3 affect the positions of x-ray source 1 and image detector 2 relative to reference frame 11 and also determining how changes in positions of each of the tracked joints (e.g. 32, 34, and 36) affect the position of reference frame 11 relative to a common imaging reference. One step in a calibration method determines positions of x-ray source 1 and image detector 2 in the coordinate space 10 with respect to reference frame 11 for various tilts and orbits of C-frame 3. In this step the position of the carriage 8 and the rest of the rigid segments (6 and 7) of the C-arm machine are kept fixed. The calibration will be performed for intervals of tilt and orbit covering the entire range of tilts and rotations in which the C-frame is expected to be used. It is not mandatory to perform the calibration for every possible combination of tilt and orbit angles in which the C-frame machine might be used since interpolation (or extrapolation) may be used to fill in tilt and orbit angles between those covered by the calibration.

This step may be performed using a GCP designed so that the coordinates of x-ray source 1 and image detector 2 relative to the fixed coordinate system 11 may be determined by image analysis. The GCP is placed at a known location relative to reference frame 11 and imaged for different tilt and orbit angles of C-frame 3. Each image or set of images may be processed to yield corresponding positions for x-ray source 1 and image detector 2. These positions (or equivalent information) may be stored along with the corresponding tilt and orbit angles of the C-frame in a calibration table. An example phantom which may be used as a GCP is described in "A low-cost tracked C-arm (TC-arm) upgrade system for versatile quantitative intraoperative imaging", *International Journal of Computer Assisted Radiology and Surgery (JCARS)* (available online; 2013 Oct. 22; DOI: 10.1007/s11548-013-0957-9) which is hereby incorporated herein by reference for all purposes.

During subsequent use of the C-arm machine the current tilt and orbit angle of the C-frame may be measured (e.g. by looking up values from inclination sensors on the C-frame or monitoring outputs of inertial sensor(s) on the C-frame), current estimated positions for x-ray source 1 and image detector 2 may then be determined by lookup in the calibration table (interpolation may be performed on values in the calibration table in cases where calibration is performed at larger intervals of tilt or orbit) for a given tilt and orbit read from sensor 31. The measured angles of tilt and orbit and/or the determined positions of x-ray source 1 and image detector 2 and/or equivalent information may be stored with and/or linked to x-ray images 29 acquired by the C-arm machine.

In some embodiments, the part of an imaging machine support structure that is being treated as a non-rigid part may include more than one joint. In such embodiments calibration information may be looked up as an N-dimensional lookup (where N is the number of joints in the non-rigid part) using sensor values indicating positions of the N joints. In other embodiments the positions of a first set of the joints is used in a first lookup to obtain calibration information specifying parameters of a virtual link 13 (e.g. directly or indirectly specifying a length and direction of virtual link 13) and positions of a second set of the joints is used in a second lookup to obtain calibration information specifying a location of an imaging head in a coordinate space fixed at the end of the virtual link. In such embodiments, different virtual links are included in the kinematic chain for different positions of the first set of joints (which may comprise one joint in some embodiments).

Another calibration step defines how changes in position of each tracked joint (as represented by sensor readings) affects the vector position of the tracked joint with respect to reference frame 11. This step may provide scaling factors and offset values that can be applied to sensor readings to convert all translations and rotations resulting from operations of the individual joints to a common reference frame (e.g. it is convenient to use reference frame 11 as the common reference frame). This calibration step may be performed for example for tracked joints in that portion of the support structure that is being treated as a rigid structure.

A SCP 14 may be used for this purpose. A SCP includes a particular arrangement of embedded radio-opaque markers so that for a given bi-planar x-ray views taken from a small area of the SCP, the position of the image with respect to a coordinate system of the SCP can be determined by analyzing the coordinates and appearance of the markers in the x-ray views. An example SCP is described in "A low-cost tracked C-arm (TC-arm) upgrade system for versatile quantitative intraoperative imaging", *International Journal of Computer Assisted Radiology and Surgery (JCARS)* (available online 2013 Oct. 22; DOI: 10.1007/s11548-013-0957-9) which is hereby incorporated herein by reference for all purposes.

Figure 4:
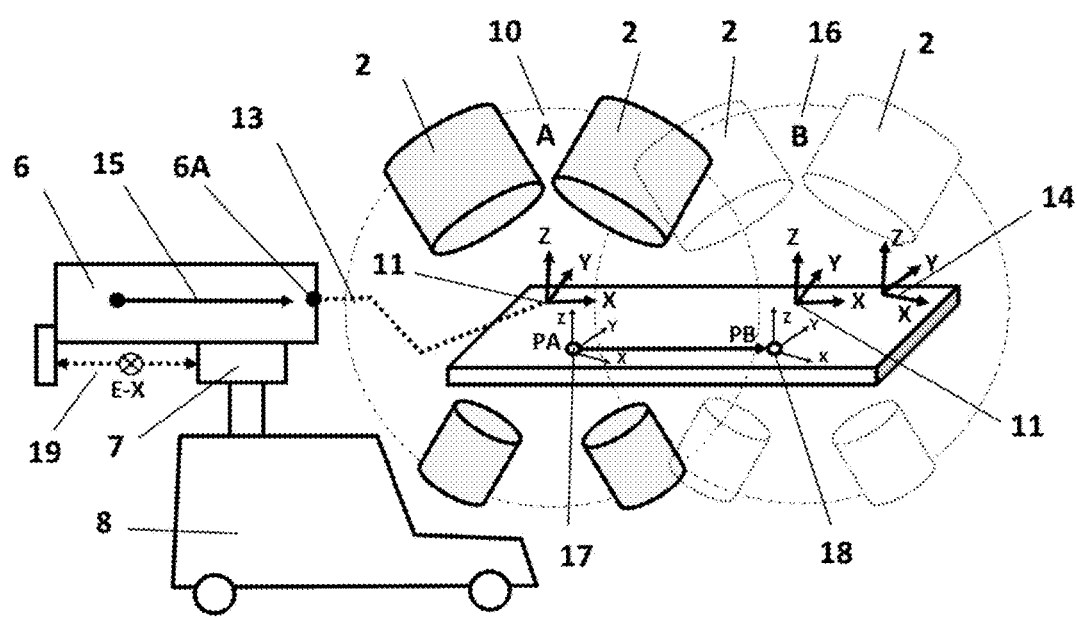
FIGS. 4, 5 and 6 are schematic side elevation views illustrating the use of a slab calibration phantom (SCP) to calibrate motions respectively of: a horizontal linear motion joint, a vertical linear motion joint and a rotational (swinging) joint.

FIG. 4 illustrates how calibration may be done for a translational joint that produces movements in a horizontal or close to a horizontal plane. For example, the joint coupling segments 6 and 7 to one another (also illustrated as 32 in FIG. 3) allows relative motion of segments 6 and 7 in a horizontal plane. Starting by placing this joint at position A, C-frame 3 can be sequentially placed at two different orientations preferably at 90° or close to 90° angular distance, for instance at +/−45° with respect to a vertical reference line. From these imaging angles, two radiographs of SCP 14 will be taken sequentially. Such images may be called 'bi-planar views'. The positions in reference frame 11 of x-ray source 1 and image detector 2 for each imaging angle may be determined as described above and associated with the corresponding image.

Given x-ray images representing two projections of SCP 14 and associated calibration information, one can determine a three-dimensional orientation and location of a local coordinate system 17 having an origin PA for the portion of the Slab Calibration phantom 14 visible in the corresponding bi-planar radiographic views. Subsequently without moving SCP 14, segment 6 can be moved horizontally as shown by 15 along the corresponding joint to position B. With C-frame 3 in this new position relative to SCP 14, another pair of bi-planar views may be obtained and a new local coordinate system 18 corresponding to the portion of SCP 14 visible in the new pair of bi-planar views will be constructed with an origin at PB and with a known relationship in respect to reference frame 11 at position B. The coordinates of both PA and PB have been determined with respect to reference frame 11. Since the vector PA to PB is known from the design of SCP 14 (with respect to the frame of reference of slab calibration 14), the corresponding three-dimensional translation vector between positions A and B with respect to coordinate space 10 associated with reference frame 11 at position A can be determined by analysis of this known information. This analysis defines the orientation of the translational joint with reference to the coordinates of the frame 11 located at position A.

If a change in the reading of the encoder 19 connected to measure movements of the corresponding joint is E–X for the distance travelled, a scale factor for relating E–X to the actual distance of the translation can be obtained by taking the ratio of the magnitude of the translation vector determined from image analysis as described above to E–X.

Figure 5:
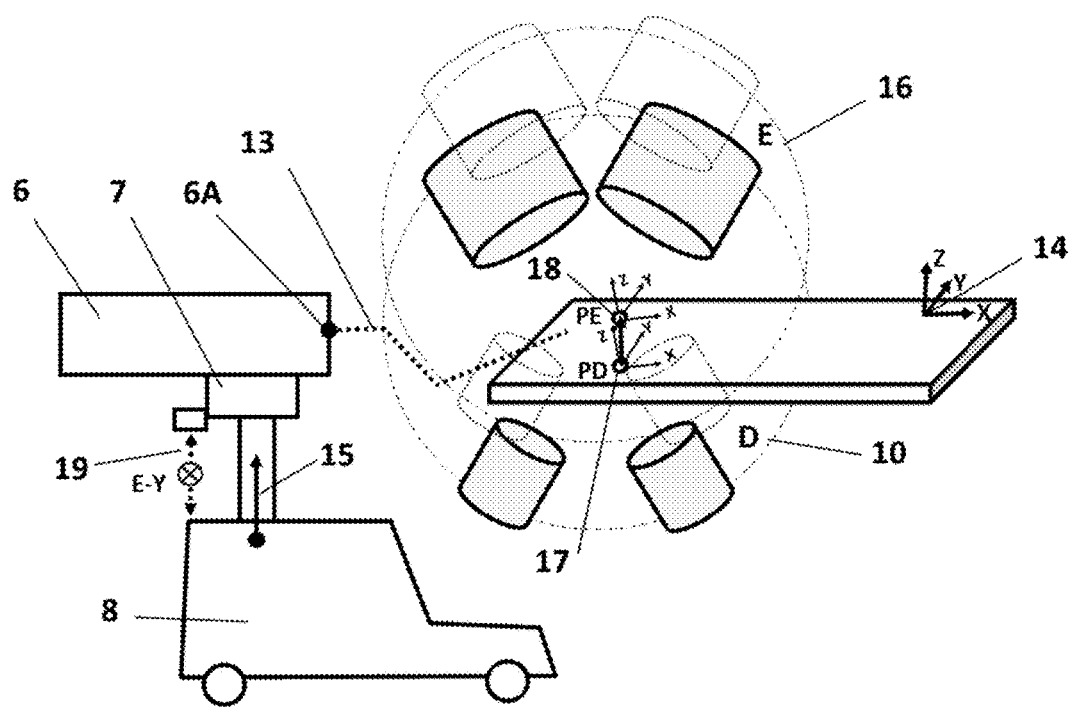

Calibration of a translation joint which allows motion in a vertical or close to a vertical direction may be performed in a similar manner as indicated for the vertical joint shown in FIG. 5. Bi-planar views of SCP 14 are again used to obtain a three-dimensional reconstruction of a local coordinate system 17 with its origin at PD, corresponding to the portion of SCP 14 visible in bi-planar radiographic views taken at position D. C-frame 3 is then raised (or lowered) to position E by operating the corresponding vertical joint. Another set of bi-planar views of SCP 14 is then acquired. From the second set of bi-planar views the frame of reference 18 with its origin at PE is reconstructed with reference to frame 11 at position E. From the geometric relationship between PD and PE (which is known from the design of SCP 14) and also the known positions of PD and PE with respect to reference frame 11 a complete three-dimensional definition of the vertical translation vector 15 can be determined with respect to the frame 11 at position D. A scale factor for readings of the sensor which encodes motions of the joint in sensor readings can then be obtained by taking a ratio of the magnitude of translation calculated for the joint by image analysis to the difference in sensor readings E–Y 19 for motion of joint Y between positions D and E.

Figure 6:
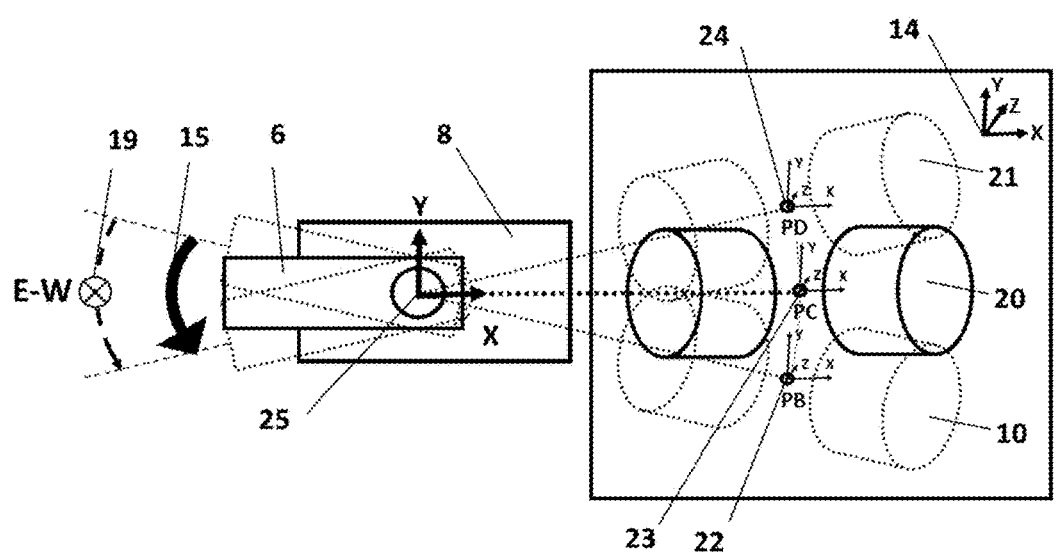

For a rotational joint, in addition to finding the vector orientation and the magnitude of a scaling factor, the calibration should also define the exact position of the vector in three dimensions. FIG. 6 is a schematic top view of the C-arm machine during calibration for illustrating an example calibration method for the rotational joint 36 of the example C-arm machine shown in FIG. 3. In calibration of this joint, sets of bi-planar views 10, 20, and 21 of SCP 14 are obtained for each of three different positions B, C, and D produced by sequentially rotating the C-arm about a vertical joint. As described above for calibration of translational joints, from pairs of bi-planar views the reference frames PB, PC, and PD are reconstructed in three-dimensions with respect to the frame of reference 11 corresponding to positions B, C, and D. From the reconstructed positions of the frames 22, 23, and 24 with origins at PB, PC, and PD corresponding to different visible portions of the SCP 14, and the known information about the relative positions of these three with respect to the design of SCP 14, the direction and exact position 25 of the axis of rotation with respect to the frame 11, as well as the true magnitude of rotation can be calculated from analysis. This may be done, for example, by fitting a circular trajectory to the three poses B, C, and D.

Calibration of a rotational joint may optionally include obtaining images of slab calibration 14 in more than three positions for further improvement of the accuracies of the circular path fitting, if necessary or desired. Ideally the poses are selected to be separated from one another by large angles (e.g. at or near the maximum angular separations allowed by the mechanical constraints and also the size of SCP 14). The read of the angular distance can be determined through various means including but not limited to mechanical, optical or electro-magnetic sensors. A scale factor for correcting readings of the angle sensor may be calculated by taking the ratio of the true magnitude of rotation found from image processing as described above to the change in output of the sensor E–W between the corresponding positions.

For all the steps of calibration above, the initial readings of the joint sensors may be stored and subsequently used as calibration reset points for zeroing offsets during the tracking and use of the device. Following the calibration of all the translational and rotational joints of the device (for example as described above), the position of reference frame 11 relative to carriage 8 can be kinematically tracked by taking the initial position of reference frame 11 as the frame of reference. For example, for the construct of the C-arm shown in FIG. 3, after calibration reference frame 11 can be tracked based on the readings of the sensors and applying the sequential translations and rotations of the joints 33, 34, and 36 in the same order. After placing the frame 11 in three dimensions, the true positions of the x-ray source 1 and the image detector 2 may be defined with respect to the final position of the frame 11 based on measurements of tilt and orbit of the C-frame using a calibration table and an interpolation function as described above.

For cases where the entire imaging machine may be moved to different positions with respect to the patient (or temporarily moved away from the patient and then brought back to the patient), the movements of carriage 8 can also be added to the kinematic chain provided that the tracking with respect to a fixed reference such as floor 9, wall or ceiling of the room is available. Tracking of the position of carriage 8 may be provided, for example, using an optical localizer or a tracker mounted underneath the carriage.

Figure 7:
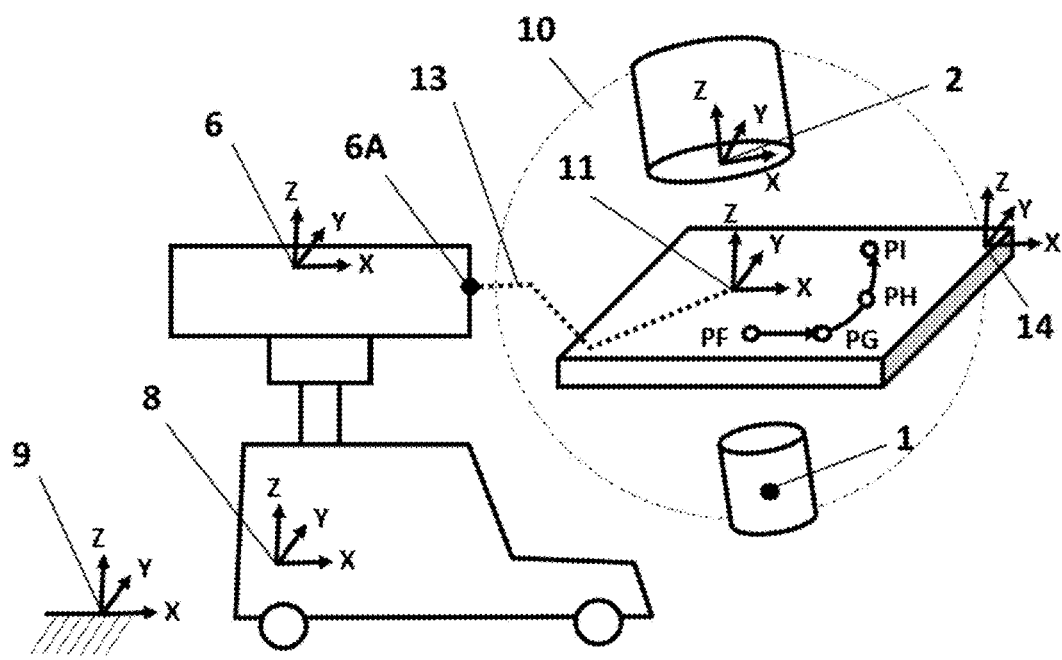
FIG. 7 is a schematic view illustrating use of a SCP to calibrate motions of a tracked carriage of a C-arm machine.

The tracking of carriage 8 may be calibrated in this case using SCP 14 as illustrated, for example, in FIG. 7. Keeping all the joints of the C-arm machine fixed, carriage 8 can be moved sequentially so that x-ray source 1 and image detector 2 image different positions along the width and depth of SCP 14. FIG. 7 shows an example maneuvering of carriage 8. At each of positions F, G, H, and I, the brakes of carriage 8 are applied and a set of bi-planar images of the SCP 14 are acquired. As described above, the bi-planar images taken at each position can be processed to yield corresponding three dimensional reconstructions of the visible portion of SCP 14. These reconstructions are illustrated at PF, PG, PH, and PI with reference to the coordinate system of reference frame 11. The geometric relationships between PF, PG, PH, and PI can be determined from the design of SCP 14. This information along with the three-dimensional tracking of carriage 8 with respect to fixed reference frame 9 may be used to construct a homogenous transformation that translates the position information of carriage 8 from its tracker reference frame 9 to the frame 11.

Similarly, in case of using a three-dimensional localizer device directly for tracking the three-dimensional position and orientation of the body segment 6 adjacent to the virtual rigid link 13, the calibration will be identical to what is described above for a moving carriage 8, with the difference that the prescribed maneuvering during calibration should also include changing in the elevation of the C-frame.

The following describes a non-limiting example embodiment. Features of this non-limiting example may also be applied individually and in combination in other contexts. A tracking system as described below may be applied to track positions of imaging machines having other constructions. For example, sensor-tracking modules as described below may be applied to position determination for virtually any C-arm system with any practical arrangement of joints and segments.

Figure 8:
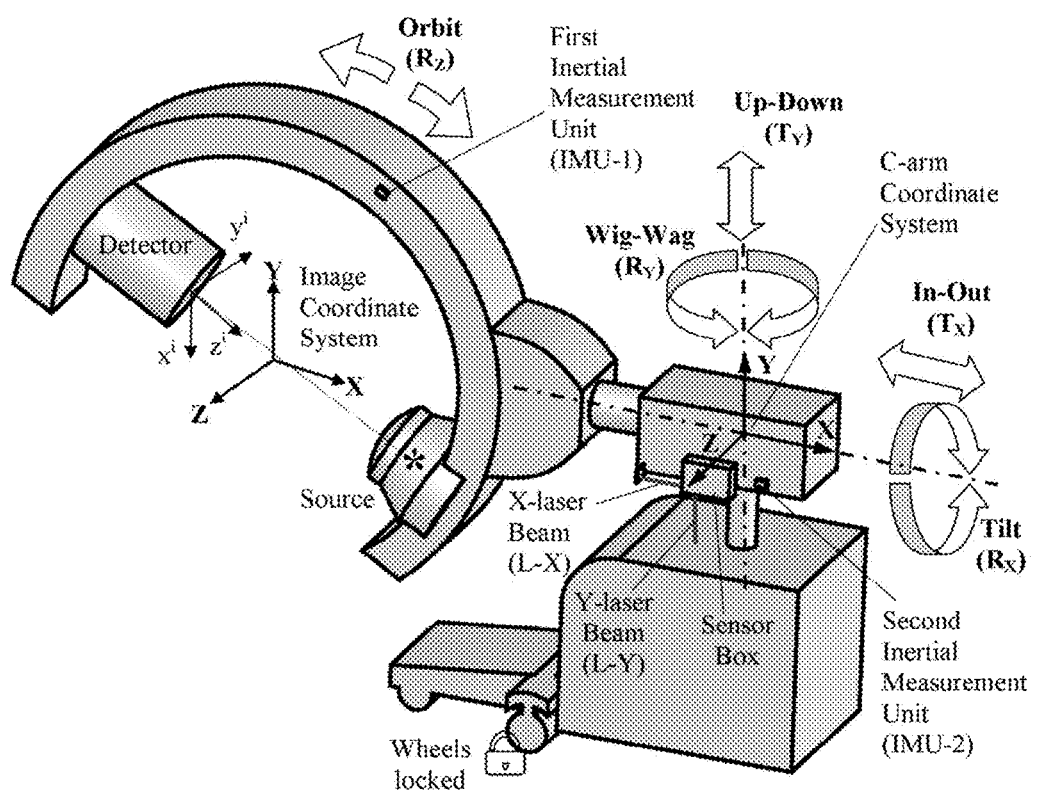
FIG. 8 is an example schematic view of a C-arm device with inertial measuring units and laser range meters to provide tracking of individual joints.
Figure 9:
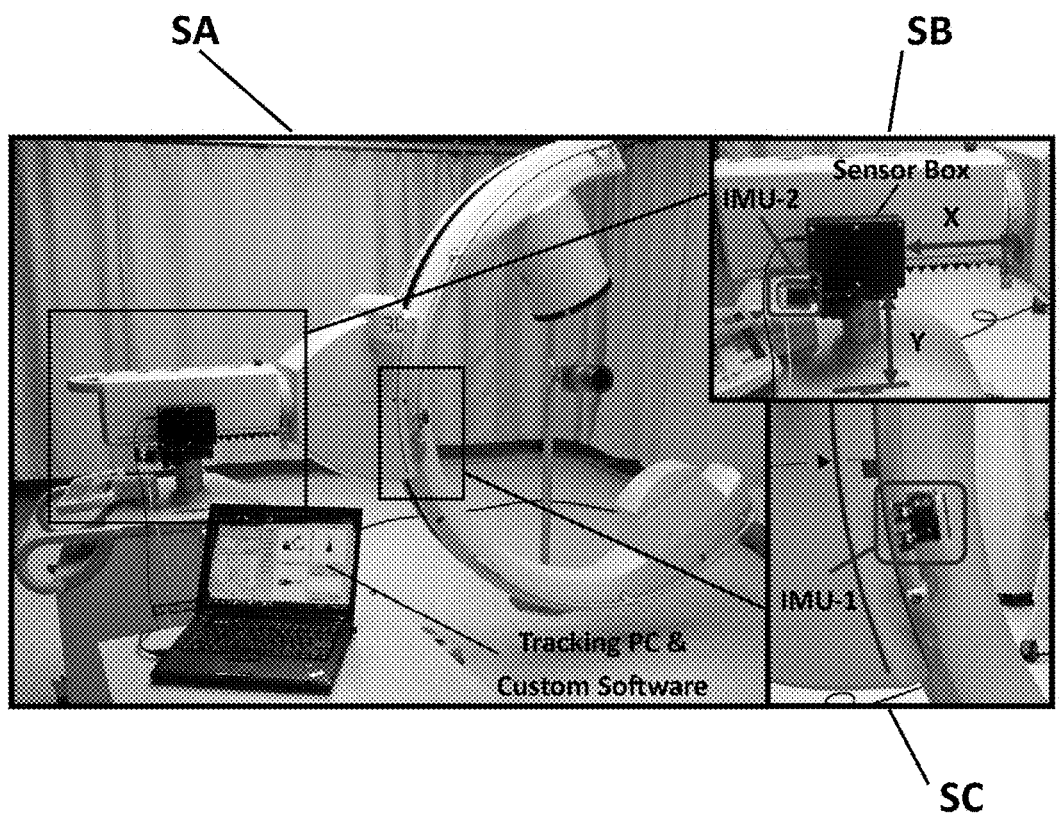
FIG. 9 is a photograph showing an example prototype embodiment.

Example Application—Instrumenting a C-Arm X-Ray Machine with Sensors:

A Siemens Arcadis Orbic™ ISO-C C-arm (Siemens AG, Munich, Germany) with a typical 5 degree-of-freedom (DOF) joint configuration as shown in FIG. 8 was instrumented to facilitate tracking changes in position of the x-ray source and detector. The instrumentation included two inertial measurement units (IMUs) and two laser distance measurement sensors. An advantage of this selection of sensors is that such sensors may be mounted to or removed from an existing C-arm machine with little or no modification of the C-arm machine and without the need to disassemble the C-arm machine. The first IMU was attached to the gantry (C-frame) (see FIG. 9-SC) to measure orbit and tilt ($R_Z$ and $R_X$ in FIG. 8). The second IMU was attached to the horizontal bearing on the C-arm (see FIG. 9-SB), and was dedicated to detecting wig-wag ($R_Y$ in FIG. 8). The laser measurement sensors were assembled into a sensor box (see FIG. 9-SA).

In the prototype embodiment the IMUs were wireless and battery-powered. The IMU sensors (X-IO Technologies, UK) are equipped with built-in algorithms for fusing data from internal gyroscope and accelerometer sensors. The IMUs have Bluetooth™ wireless capability for communicating near-to-real-time absolute orientation measurements to a PC or other controller.

Figure 10:
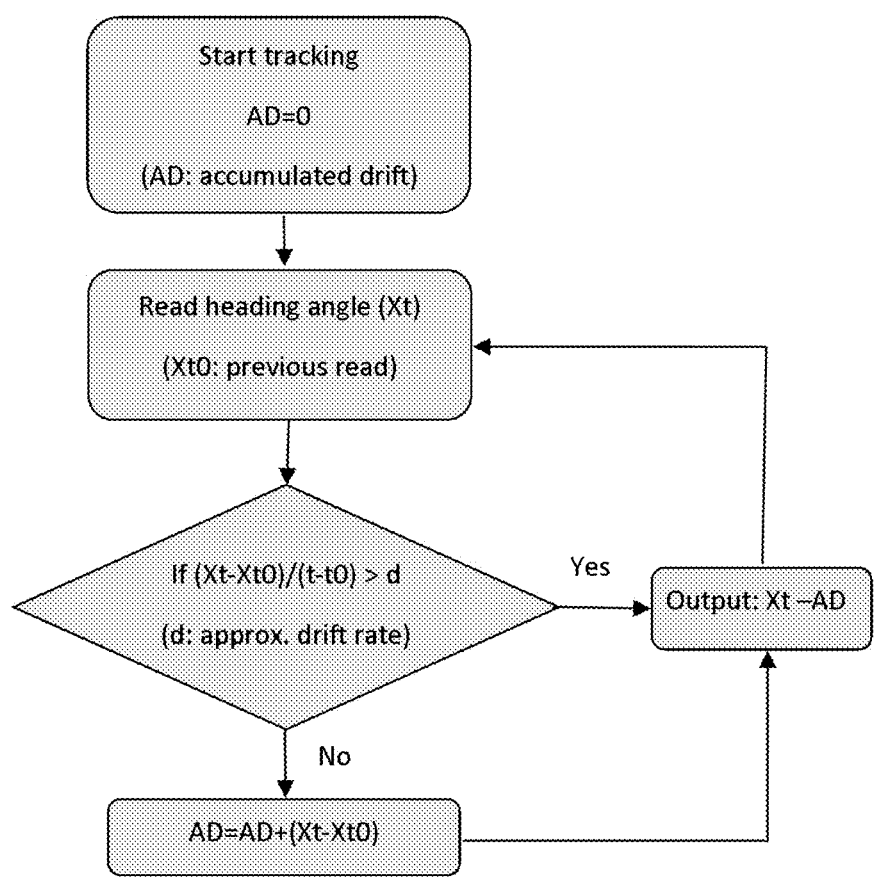
FIG. 10 is a flow chart illustrating a method for reading an intertial sensor which compensates for drift in the sensor output signal.

IMU sensors can tend to drift, especially when used to measure rotation about a vertical axis. Such drift can be compensated for by processing output from the IMU using a drift-cancellation algorithm. The drift-cancellation algorithm may be incorporated into a data acquisition system. An example drift-cancellation algorithm (FIG. 10) monitors wig-wag angle measurements from the IMU sensor and filters out a component of drift detected as a continuous and gradual change of orientation in the horizontal plane.

In the prototype, the sensor box provides measurements of the gantry movements (FIG. 9SC) about the horizontal and vertical axes ($T_X$ and $T_Y$ in FIG. 8) through two analog laser distance sensors (OADM 20S4570/S14F, Baumer GmbH, Friedberg, Germany). Data from the distance sensors is communicates to the tracking PC through a suitable wired or wireless data link. In the prototype a RS485 interface and a USB port converter (FIG. 9SA) were used to transmit the distance data to a PC that was used as a data acquisition system and tracking controller.

Figure 11:
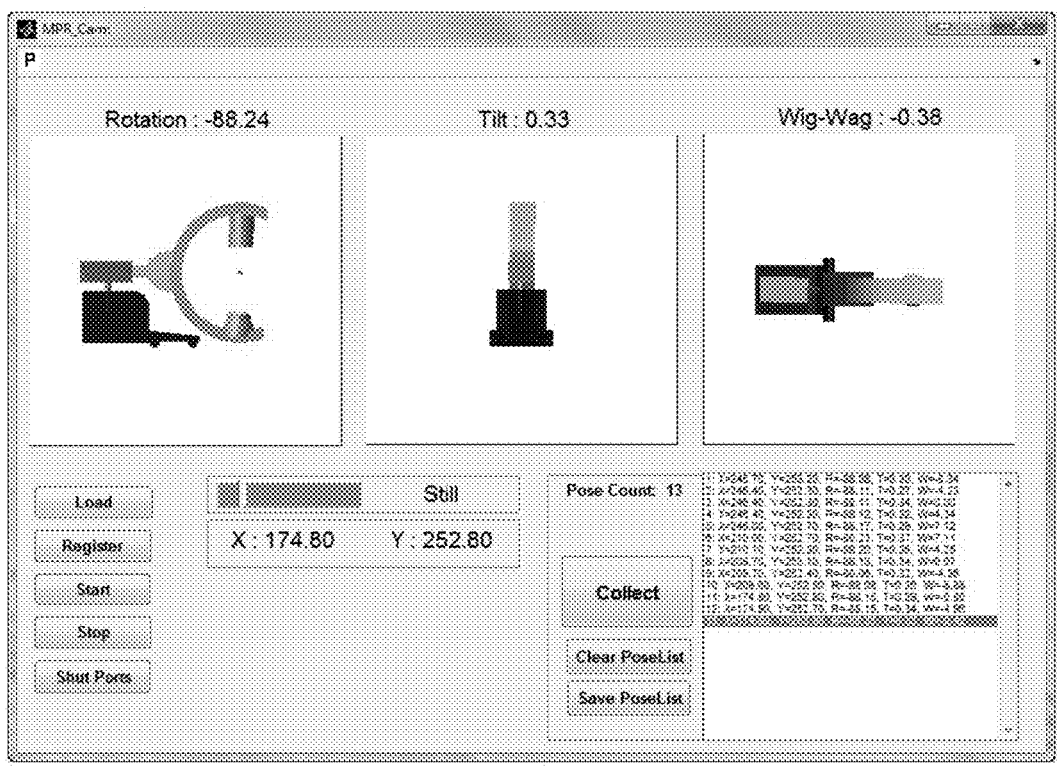
FIG. 11 shows a display in a user interface of a prototype example embodiment.

Custom software for tracking the C-arm (FIG. 11) was developed using the MATLAB® R2012a software (MathWorks Inc, Natick, Mass., USA).

The prototype is a specific example of the more general concept that an imaging device having a number of movable joints can be instrumented in a way that permits suitably accurate position determination using a kinematic chain model of the imaging device with sensors that can be surface-mounted to the imaging device (i.e. without requiring any significant disassembly or modifications to the imaging device itself). The prototype also demonstrates the following concepts:

inertial sensors (e.g. IMUs) or accelerometers may be applied to monitor changes in the angles of rotary couplings between segments of an imaging machine, particularly tilt and orbit of a gantry such as a C-arm.

distance measuring units (for example laser distance transducers) may be applied to monitor positions of translating (sliding) joints.

sensors in these applications may be configured to communicate wirelessly with a data acquisition system or controller.

Forward Kinematic Model of the C-Arm:

The position of the gantry of an imaging device such as a C-arm machine can be tracked using a sequence of transformations that correspond with different joints and body segments of the C-arm as illustrated by the following example equation:

$$[T]=[T_{RY}]\times[T_Y]\times[T_X]\times[T_{RZ,RX}] \qquad \text{Equation. 1}$$

In this example, [.] represents a transformation. In some embodiments the transformation is represented in the form of a matrix (e.g. a 4×4 matrix) having elements which represent rotations and/or translations. Equation 1 corresponds to the case of an imaging machine having a support structure that includes joints that permit rotation about a vertical axis which corresponds to the transformation $[T_{RY}]$, displacement in a vertical direction which corresponds to the transformation $[T_Y]$, displacement in a horizontal direction which corresponds to the transformation $[T_X]$ and orbit and tilt of a C-frame or gantry in addition to the mechanical deformation of the C-frame which together correspond to the transformation $[T_{RZ,RX}]$.

Equation 1 may be used, for example, to track the position of the end 6A of segment 6 to which C-frame 3 is attached in the embodiment illustrated in FIG. 3.

Parameter values for each transformation may be determined based on the positions of the joints corresponding to the transformations. For example, the transformations may be determined from orbit and tilt angles (e.g. $T_{RZ,RX}$ from inertial sensor IMU-1), horizontal and vertical translations (e.g. $T_X$ and $T_Y$ which may be measured by laser distance sensors) and wig-wag angle (e.g. $T_{RY}$ from the inertial sensor IMU-2) (detailed illustrations of directions of motion of the various joints in an example support structure for a C-arm x-ray machine are shown in FIG. 8).

To facilitate using measurements of joint configurations to track the position of an imaging head such as an x-ray source/detector one can register the mounted orientation of the IMU sensors with respect to the body of the C-arm and calibrate the system in order to establish relationships between tracking and imaging domains.

Registering the IMUs:

Registration may be performed when the sensor system is initialized (e.g. at the beginning of a surgical case). Registration may be performed, for example, by moving joints of an imaging machine in a specific sequence. The following is one example of a possible calibration sequence. This example sequence of motions may be used to initialize IMUs in a C-arm machine having a structure like that shown in FIG. 8. Initialization of the IMUs establishes the spatial relationships between a coordinate system on the base of the C-arm and the coordinate system local to the IMUs.

A. Position the gantry at a predetermined position, for instance at zero orbit, zero tilt, and minimum wig-wag angle (Position RA);
B. Change the wig-wag angle of the gantry. For example swing the gantry to a maximum wig-wag angle in a predetermined (e.g. a clockwise direction when viewed from above) (Position RB);
C. Change the orbit angle of the gantry in a predetermined direction (e.g. the clockwise direction) (Position RC);
D. Bring the C-arm to a desired reset point (e.g. a configuration in which orbit, tilt and wig-wag angles are set to zero (Position RD).

Orientations of the orbit axis ($T_Z$) and wig-wag axis ($T_Y$) in a tracking coordinate system are calculated from analyzing transformation matrices formed from orientation outputs of the IMU sensors at positions RA, RB, and RC (Eq. 2; Eq. 3). Orientation of the tilt axis ($T_X$) is defined as the cross-product of the Y and Z axes. Position RD may be used as a zero reference for all angle measurements after registration.

$$[R_Y]=[T_{RB}]_{IMU1} \times [T_{RA}]^{-1}_{IMU1} \qquad \text{Equation. 2}$$

$$[R_Z]=[T_{XC}]_{IMU2} \times [T_{RB}]^{-1}_{IMU2} \qquad \text{Equation. 3}$$

Example of Tracking Software

In an example prototype embodiment custom software communicates with the sensors, registers the C-arm axes, and collects snapshots of sensor data at positions that correspond with the images acquired by the system. The custom software provides a graphical interface for visualization and tracking of the current position of the C-arm (see FIG. 11). To acquire sharp fluoroscopic snapshots with minimum blur, and to avoid unreliable position data caused by vibration, the software signals to the user when all the vibrations in the machine are damped (the software may determine this by waiting until outputs from the sensors which monitor joint positions stabilize and/or by monitoring outputs of one or more vibration sensors attached to the gantry or other portion of the C-arm machine. Damping of vibrations typically occurs within a couple of seconds of stopping the C-arm at a given position.

Gantry Calibration

Figure 12:
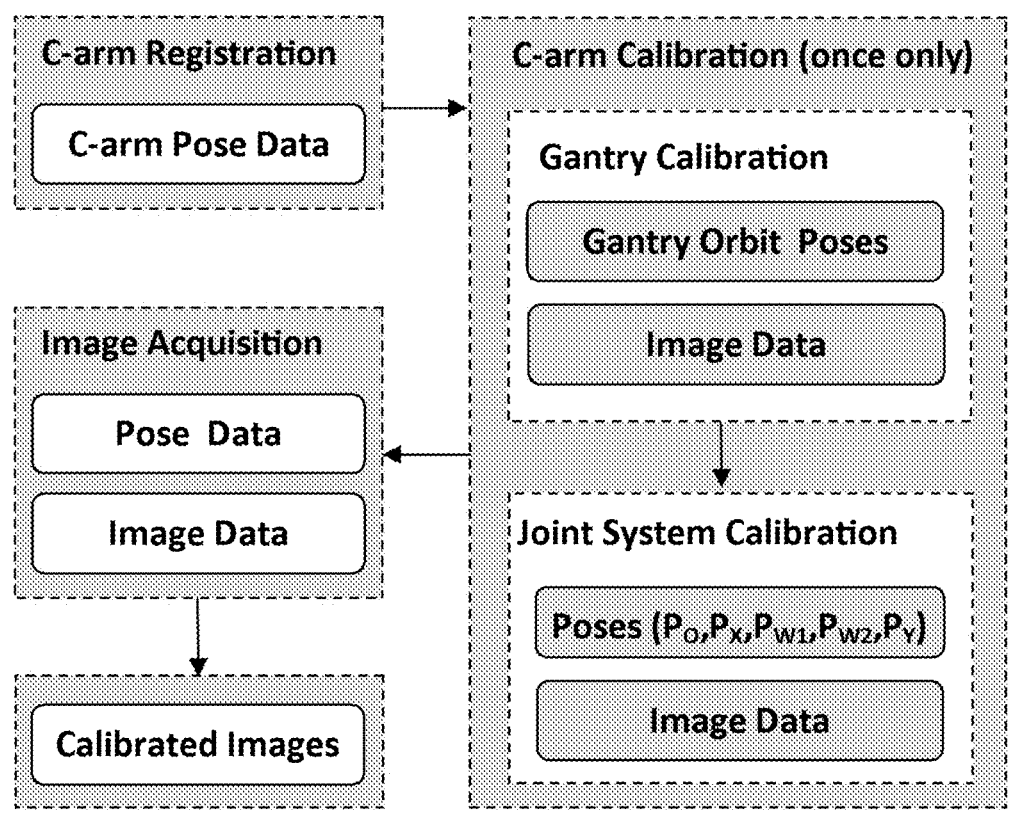
FIG. 12 is a diagram illustrating data flow in an example workflow including registration, calibration and image acquisition stages.

Calibration may be performed in two stages: (i) Gantry Calibration, and (ii) Joint System Calibration. An example calibration workflow is illustrated in FIG. 12. Calibration may be performed and calibration information recorded such that calibration can be conducted once after mounting the sensors on the device and the calibration data can subsequently be used without the need to repeat the calibration. The Joint System Calibration may needed to be repeated if the mounting fixation of the translational sensors (e.g. the Sensor Box in FIG. 9) are displaced.

Gantry Calibration

Figure 13A:
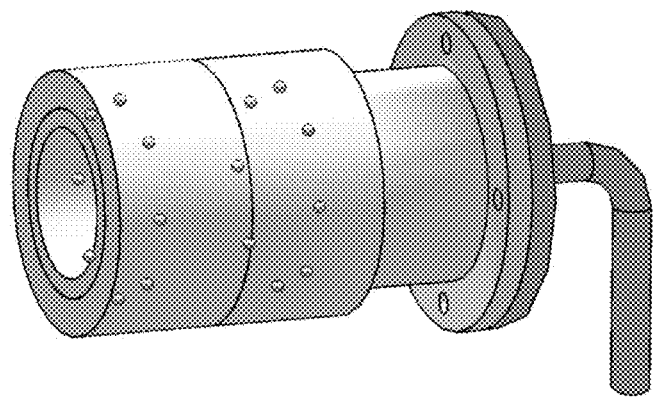
FIG. 13A illustrates an example gantry calibration phantom.
Figure 13B:
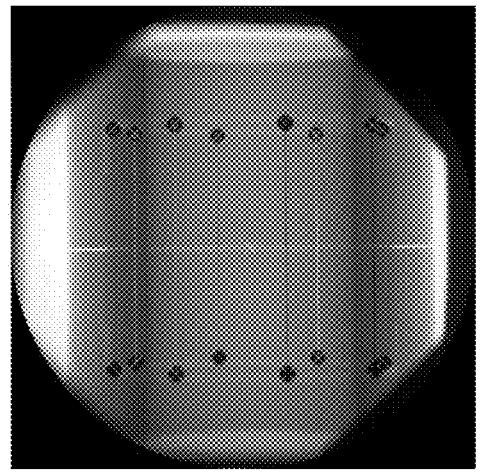
FIG. 13B is a radiograph of an example gantry calibration phantom.

Gantry calibration involves orbiting the gantry in small increments (e.g. increments of 2 to 8 degrees; 5° increments was used in the example prototype embodiment) at a fixed tilt angle and acquiring radiographs of a structure having a known geometry (e.g. a cylindrical GCP (see FIG. 13A) for the full range of rotation of the gantry (e.g. 190° for the C-arm used in this example). Sensor data (e.g. output of IMU-1) is acquired for the corresponding imaging positions. Images of the imaged object (e.g. the GCP) are processed to estimate the intrinsic and extrinsic imaging parameters (which define the position of the x-ray source and detector) from radiographic projections (FIG. 13B) as described, for example in Daly et al., 2008, Geometric Calibration Of A Mobile C-Arm For Intraoperative Cone-Beam Ct. Med. Phys. 35(5):2124-2136; Cho et al., 2005, Accurate Technique For Complete Geometric Calibration Of Cone-Beam Computed Tomography Systems. Med. Phys. 32(4):968-983; and Amiri et al., 2011, A Novel Multi-Planar Radiography Method for Three Dimensional Pose Reconstruction of the Patellofemoral and Tibiofemoral Joints after Arthroplasty. J. Biomech. 44(9):1757-1764, all of which are hereby incorporated herein by reference.

The image analysis results of all the radiographic projections along with a cubic interpolation function "ƒ" in Eq. 4 return the imaging parameters for any desired orbit ($R_Z$) (Eq. 4). Since the deformation of the C-arm also depends on the tilt angle of the C-arm ($R_X$), the calibration process may be repeated for various tilt angles. For example, the orbiting of the C-arm may be repeated at increments of tilt angles spanning the desired range within which the C-arm will be manoeuvred in its final application.

$$[T_{RZ}, R_X] = f(R_Z, R_X) \qquad \text{Equation. 4}$$

Joint System Calibration

Figure 14A:
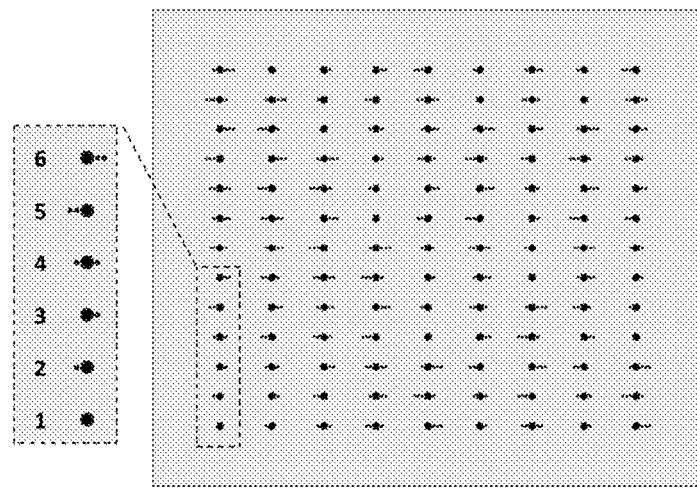
FIG. 14A is a plan view of an example slab calibration phantom.

Joint System calibration uses a SCP that includes a plurality of distinguishable features that are at known positions in the SCP with respect to one another. In an example embodiment, the SCP comprises a rectangular matrix (e.g. 370 mm by 320 mm in a prototype embodiment) of steel ball bearings. The steel ball bearings are of different sizes and are arranged in patterns that differ with position in the SCP such that views of different areas on the SCP can be distinguished from one another by image analysis. In the prototype embodiment, ball bearings of different sizes (e.g. 4.8 and 1.6 mm in diameter) were arranged in distinctive patterns (FIG. 14A). The row and column of each ball bearing could be determined from the pattern of sizes of other ball bearings in its immediate vicinity.

Figure 14B:
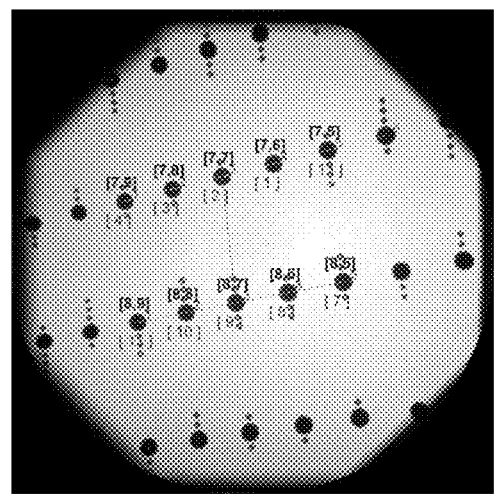
FIG. 14B is one of a pair of views of a portion of a slab calibration phantom and illustrates the principle of three-dimensional triangulation of the location of three markers identified from bi-planar views of the slab calibration phantom.

The features in images of the SCP may be detected automatically by segmenting any radiographic projection of the phantom (FIG. 14B). In an example embodiment Joint System calibration involves acquiring a pair of oblique radiographic views (separated by about a 90° angle about the orbit axis) of the fixed SCP at each of a plurality of locations on the SCP. Movements of the X-ray source and detector to obtain these radiographic views may be achieved by moving the C-arm joints in a particular order.

In an example embodiment, calibration includes:
A. Moving the C-arm to an initial 'zero' position (e.g. Position 'PA');
B. Then moving the C-arm along the horizontal $T_X$ axis shown in FIG. 9 (e.g. to Position 'PB');
C. Then swinging the C-arm by changing the wig-wag angle about the axis $T_Y$ shown in FIG. 9 by an increment of e.g. a few degrees (a 4° increment is suitable in some cases) (e.g. to Position 'PC');
D. Then swinging the C-arm by an additional increment in the wig-wag angle about the $T_Y$ axis (e.g. swinging the C-arm through an additional 4° increment with respect to the previous pose (e.g. to Position 'PD'); and E. Then raising or lowering the C-arm gantry along the vertical axis $T_Y$ shown in FIG. 9 (e.g. to Position 'E').

The increment selected for changes in the wig-wag angle may be chosen based on the size of the SCP such that the x-ray source and detector can image an area of the SCP in each pose.

Figure 15:
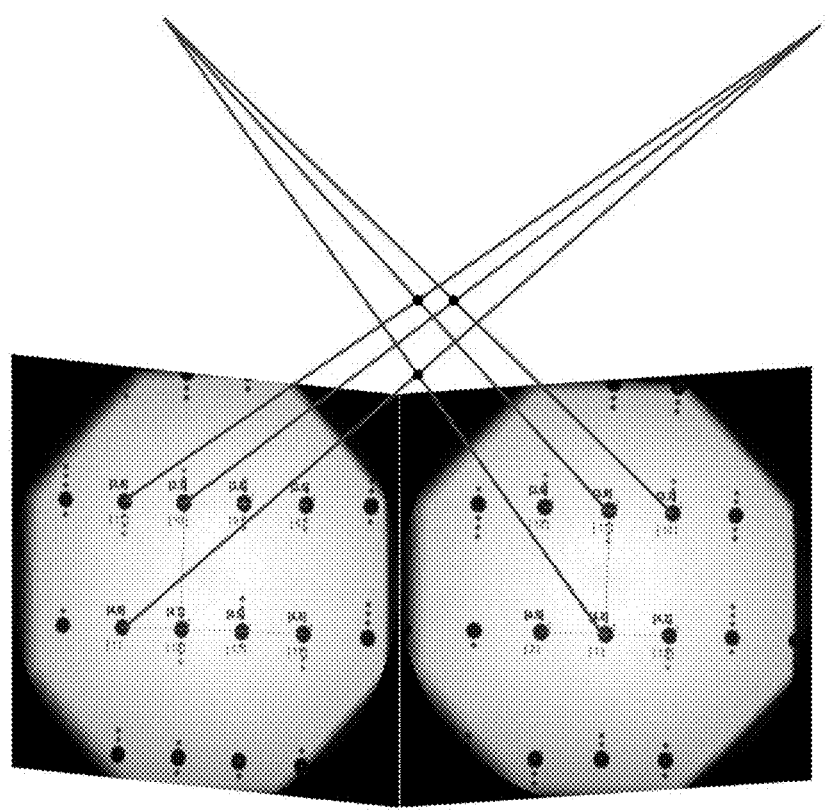
FIG. 15 illustrates a process for reconstructing a slab calibration phantom (i.e. determining positions of features of the slab calibration phantom and an orientation of the slab calibration phantom) from a pair of bi-planar views of the slab calibration phantom.
Figure 16:
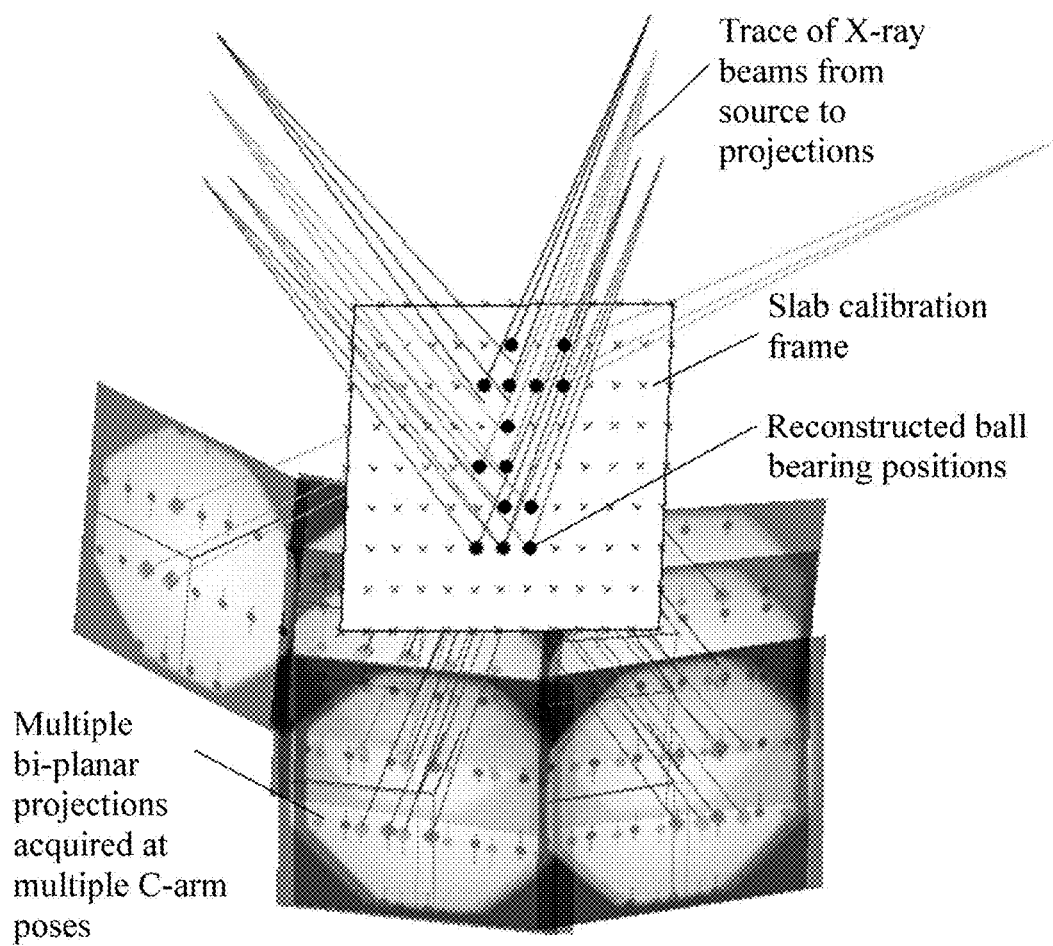
FIG. 16 illustrates how a plurality of pairs of bi-planar views of a slab calibration phantom acquired at multiple poses of a C-arm (each pair of bi-planar views may be processed as illustrated by FIG. 15) can yield information regarding the trajectories followed when joints are moved.

A pair of radiographs of the SCP is acquired for each pose. Each pair of radiographs acquired during the joint system calibration is analyzed by the calibration software to automatically reconstruct the three-dimensional locations of three ball-bearings identified in both images of the radiographic pair (FIG. 15) based on the segmented locations on the images of the ball bearings and the corresponding intrinsic and extrinsic parameters found from Gantry calibration (Eq. 4). The results are then used to determine the corresponding transformation matrices ($T_{PA}$, $T_{PB}$, $T_{PC}$, $T_{PD}$, and $T_{PD}$) that describe the phantom position with respect to the gantry for each of the imaging positions (FIG. 16), and consequently to find the direction vectors $V_X$, $V_Y$, and $V_W$ for motions of each of the axes $T_X$, $T_Y$, and $R_Y$ (Eq. 5, Eq. 6, Eq. 7, Eq. 8) of the device (FIG. 8). In these equations, function $f_{translate}$ returns the translation vector component; function $f_{rotate}$ returns a rotation vector, a point on the axis, and the corresponding magnitude of rotation that describes the motion between the three input positions.

The analysis yields calibration coefficients that account for inevitable misalignments between the mounted positions of the sensors and the ground truth axes of the C-arm found from image analysis all with respect to a common imaging reference frame. The coefficients $K_X$, $K_Y$, and $K_W$ in the analysis (Eq. 5, Eq. 6, Eq. 7, Eq. 8) correspond to the horizontal and vertical distance sensors and the second IMU, respectively. E–X, E–Y, and E–W in these equations respectively correspond with the readings of the horizontal and vertical distance sensors and the second IMU:

$$K_X * \vec{V}_X * (E\text{-}X_{PB} - E\text{-}X_{PA}) = f_{translate}([T_{PB}] - [T_{PA}]) \quad \text{Equation 5}$$

$$K_Y * \vec{V}_Y * (E\text{-}Y_{PE} - E\text{-}Y_{PD}) = f_{translate}([T_{PE}] - [T_{PD}]) \quad \text{Equation 6}$$

$$\left\{ \begin{array}{l} \text{axis vector: } \vec{V}_W \\ \text{point on axis: Point}_W \\ \text{angle of rotation: } Mag_W \end{array} \right\} = f_{rotate}([T_{PB}], [T_{PC}], [T_{PD}]) \quad \text{Equation 7}$$

$$K_W = Mag_W / (E\text{-}W_{PD} - E\text{-}W_{PB}) \quad \text{Equation 8}$$

The results of calibrations may subsequently be used to generate transformation matrices (Eq. 9, Eq. 10, Eq. 11) that can be input into the kinematic model of the C-arm (Eq. 1) for determining the current position of the gantry from sensor information. The 'Translate' and 'Rotate' functions in Eq. 9, Eq. 10, Eq. 11 return the corresponding transformation matrices for the given set of sensor data (E–X, E–Y, and E–W) using the calibration parameters ($K_X$, $V_X$, $K_Y$, $V_Y$, $V_W$, Point $_W$, and $K_W$).

$$[T_X] = \text{Translate}(K_X * \vec{V}_X * E\text{-}X) \quad \text{Equation 9}$$

$$[T_Y] = \text{Translate}(K_Y * \vec{V}_Y * E\text{-}Y) \quad \text{Equation 10}$$

$$[T_{RY}] = \text{Rotate}(\vec{V}_W, \text{Point}_W, K_W * E\text{-}W) \quad \text{Equation 11}$$

Image Acquisition

After registration (which typically takes about 30 seconds) and one-time calibration, the C-arm is ready for image acquisition. The software performs tracking of the motions of the device and recording snapshots of sensor data for the corresponding imaging positions, as described previously. This paired set of sensor pose and image data may then be processed along with the calibration data (FIG. 12) to adjust the intrinsic and extrinsic imaging parameters for each collected radiograph according to the sensor data (Eq. 1).

Kit Embodiments

Some embodiments provide apparatus that may be added to an existing imaging machine to track positions of an imaging head in the imaging machine. For example, the apparatus may comprise a controller comprising a processor configured to perform tracking in any of the manners described herein. Configuration of the processor may for example be provided by a data store comprising software instructions which, when executed by the processor cause the processor to perform tracking methods, calibration methods or both tracking and calibration methods as described herein. In other embodiments some or all functions of the controller are provided by appropriate logic circuits.

The apparatus may additionally comprise sensors for sensing positions of joints in an imaging machine and wired or wireless interface components for communicating output signals from the sensors to the controller. In some embodiments the sensors comprise inertial sensors. In some embodiments the sensors comprise a battery-powered wireless sensor that can be attached to a C-frame to wirelessly communicate signals representative of tilt and orbit angles of the C-frame to the controller. In an example embodiment, the sensors comprise first and second inertial sensors and first and second non-contact linear position sensors configured for attachment to joints of a C-arm imaging machine as described herein. In some embodiments the linear position sensors are mounted together at right angles to one another in a unit that permits them to be mounted together onto an imaging machine as a single assembly. The linear sensors may, for example, comprise laser distance sensors.

In other embodiments a kit comprises a medium comprising computer software which can be executed by a processor in a customer-supplied computer and, when so executed, causes the customer-supplied computer to perform tracking methods, calibration methods or both tracking and calibration methods as described herein. Such a kit may also include one or more sensors as described above.

In other embodiments (including any of the above embodiments) a kit may comprise sensors and instructions for attaching the sensors to an imaging machine, for example, a C-arm x-ray machine. The kit may additionally comprise one or more of: a controller, a medium containing computer software instructions for execution by a computer that cause the computer to perform functions of a controller as described herein (e.g. one or more of tracking positions of an imaging head calibration, associating images with tracking information, etc.); and instructions for downloading or otherwise obtaining such software.

Kits in any of the embodiments described above may include one or more calibration phantoms (e.g. a SCP, a phantom which can be used as a SCP or a GCP or both a SCP and a GCP).

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Software and other modules may reside on servers, workstations, personal computers, tablet computers, x-ray system controllers, and other devices suitable for the purposes described herein.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention.

This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for tracking changes in a position and orientation of an x-ray source and detector in an x-ray machine comprising a movable carriage, an x-ray source and an x-ray detector and one or more sensors, the one or more sensors including a tracking system operative to sense a position of a tracked location on the x-ray machine wherein the x-ray source and detector are movably coupled to the carriage by an arm comprising a plurality of joints such that the x-ray source and detector are linked to a fixed reference frame of the tracking system by a kinematic chain, the method comprising:
using the x-ray source and detector to obtain a plurality of bi-planar views of a calibration phantom, wherein the plurality of bi-planar views correspond to a plurality of different configurations of the arm and a plurality of positions for the carriage;
processing the plurality of bi-planar views to determine changes in the positions and orientations of the x-ray source and detector resulting from changes in the configuration of the arm among the different configurations and changes in the position of the carriage;
processing the changes in positions and orientations of the x-ray source and detector to identify axes of motion of the joints and to calibrate the tracking system;
for at least one of the sensors, registering an orientation and/or position of the sensor relative to the x-ray machine by processing outputs of the at least one of the sensors for plural configurations of the kinematic chain;
constructing a transformation comprising a kinematic chain model of the kinematic chain, the transformation determining positions and orientations of the x-ray source and the x-ray detector relative to the fixed reference frame based on the outputs of the one or more sensors; and
determining the position and orientation of the x-ray source and detector relative to the fixed reference frame after a change in the position of the carriage and/or a change in configuration of the arm using the transformation and the outputs of the one or more sensors.

2. The method according to claim 1 wherein obtaining the plurality of bi-planar views comprises moving one of the plurality of joints to different positions while keeping other ones of the plurality of joints fixed and obtaining one of the biplanar views for each of the different positions of the one of the plurality of joints.

3. The method according to claim 2 comprising processing the bi-planar views for the different positions of the one of the plurality of joints to yield a vector corresponding to the axis of motion of the one of the joints.

4. The method according to claim 3 wherein the one of the joints is a rotary joint and the method comprises fitting an arc to positions corresponding to the biplanar views for the different positions of the one of the plurality of joints and setting the vector to extend along an axis of the arc.

5. The method according to claim 1 wherein obtaining the plurality of bi-planar views comprises moving each of at least two of the plurality of joints to plural different positions while keeping other ones of the plurality of joints fixed and obtaining biplanar views for the different positions of the at least two of the plurality of joints.

6. The method according to claim 1 wherein constructing the transformation comprises steps including:
reconstructing a portion of the calibration phantom that is visible in the bi-planar views and calculating a homogenous transformation between coordinates in a frame of reference in which the calibration phantom has a known position and orientation and coordinates in the fixed frame of reference.

7. The method according to claim 1 wherein the axes of motion of the joints comprise a wig-wag axis.

8. The method according to claim 1 wherein providing the plurality of sensors comprises removably attaching one or more of the sensors to the x-ray machine.

9. The method according to claim 8 wherein the tracking system comprises an optical localizer that tracks positions of targets mounted on the x-ray machine.

10. The method according to claim 8 wherein at least some of the sensors comprise battery-powered wireless sensors.

11. The method according to claim 1 comprising defining a first coordinate system by setting first and second axes of the first coordinate system to coincide with first and second ones of the axes of motion of the joints and setting a third axis of the first coordinate system to coincide with a cross product of vectors oriented along the first and second ones of the axes of motion of the joints.

12. The method according to claim 11 wherein providing the plurality of sensors comprises removably attaching one of the sensors to a member of the arm that is adjacent to one of the plurality of joints that is a rotary joint operable to rotate about an axis.

13. The method according to claim 12 comprising establishing a spatial relationship between the first coordinate system and a coordinate system local to the one of the sensors.

14. The method according to claim 13 wherein establishing the spatial relationship between the first coordinate system and the coordinate system local to the one of the sensors comprises moving the rotary joint through an angle and processing outputs of the one of the sensors before and after moving the rotary joint through the angle to determine a direction of the axis of the rotary joint in the coordinate system local to the one of the sensors.

15. The method according to claim 14 wherein the one of the sensors comprises an inertial measurement unit (IMU).

16. The method according to claim 11 comprising establishing a spatial relationship between the first coordinate system and a coordinate system local to one of the sensors by analyzing an output of the one of the sensors while moving one or more of the joints of the arm one at a time.

17. The method according to claim 1 comprising, after a change in configuration of the arm, automatically monitoring vibrations in the x-ray machine and signaling a user when the vibrations in the x-ray machine are damped.

18. The method according to claim 1 comprising displaying the determined position and using the displayed determined position to guide adjustment of the carriage and arm to position the x-ray source and detector in a desired pose relative to a subject.

19. The method according to claim 1 comprising acquiring an x-ray image using the x-ray source and detector and linking to the x-ray image the determined position and orientation of the x-ray source and detector.

20. The method according to claim 1 comprising removably affixing surface-mounted sensors to the x-ray machine, each of the surface-mounted sensors operable to sense positions of a corresponding one or more of the mechanical joints.

21. A method according to claim 1 comprising:
one at a time, moving each of the joints among a plurality of joint positions, while recording an output signal from a corresponding one of the sensors;
analyzing the recorded sensor output signals to yield a vector corresponding to each of the joints, the vector corresponding to a translational joint indicating a direction of a translational motion of the joint in the local coordinate system of the corresponding sensor, the vector corresponding to a rotational joint indicating an axis of a rotational motion of the rotational joint in the local coordinate system of the corresponding sensor;
analyzing the vectors for one or more of the joints to yield a transformation matrix that relates the output signal for the corresponding sensor to corresponding translations or rotations of the joints.

22. A method according to claim 1 wherein constructing the transformation comprises constructing a first transformation that translates position and orientation information from a reference coordinate system of the tracking system to a coordinate system fixed relative to the tracked location.

\* \* \* \* \*